(12) United States Patent
Zhang et al.

(10) Patent No.: US 8,603,734 B2
(45) Date of Patent: Dec. 10, 2013

(54) BIOMARKERS FOR PROSTATE CANCER

(75) Inventors: Hui Zhang, Baltimore, MD (US); Yan Li, Middle River, MD (US); Lori J. Sokoll, Owings Mills, MD (US); Zhen Zhang, Dayton, MD (US); Daniel W. Chan, Clarksville, MD (US)

(73) Assignee: The Johns Hopkins University, Baltimore, MD (US)

( * ) Notice: Subject to any disclaimer, the term of this patent is extended or adjusted under 35 U.S.C. 154(b) by 636 days.

(21) Appl. No.: 12/663,191

(22) PCT Filed: Jun. 4, 2008

(86) PCT No.: PCT/US2008/065782
§ 371 (c)(1),
(2), (4) Date: Jun. 14, 2010

(87) PCT Pub. No.: WO2008/151238
PCT Pub. Date: Dec. 11, 2008

(65) Prior Publication Data
US 2010/0255472 A1    Oct. 7, 2010

Related U.S. Application Data

(60) Provisional application No. 60/933,020, filed on Jun. 4, 2007.

(51) Int. Cl.
*C12Q 1/00* (2006.01)
*G01N 24/00* (2006.01)

(52) U.S. Cl.
USPC .............................................. 435/4; 436/173

(58) Field of Classification Search
None
See application file for complete search history.

(56) References Cited

U.S. PATENT DOCUMENTS

| | | | |
|---|---|---|---|
| 2004/0018519 A1* | 1/2004 | Wright, Jr. | 435/6 |
| 2005/0287610 A1* | 12/2005 | Clements | 435/7.23 |
| 2006/0269971 A1 | 11/2006 | Diamandis | |
| 2007/0099251 A1 | 5/2007 | Zhang et al. | |

FOREIGN PATENT DOCUMENTS

| | | | |
|---|---|---|---|
| JP | 2006153499 A | * | 6/2006 |
| WO | WO 2005114221 A2 | * | 12/2005 |
| WO | WO 2006130689 A2 | * | 12/2006 |

OTHER PUBLICATIONS

Baker et al., Br. J. Cancer, 1994, 70(3): 506-512.*
Freedland et al., "Loss of CD10 (Neutral Endopeptidase) is a Frequent and Early Event in Human Prostate Cancer", The Prostate, 2003, vol. 55, pp. 71-80.
Connelly et al., "Neutral Endopeptidase 24.11 in Human Neutrophils: Cleavage of Chemotactic Peptide", PNAS, 1985, vol. 82, pp. 8737-8741.

* cited by examiner

*Primary Examiner* — Hong Sang
(74) *Attorney, Agent, or Firm* — Johns Hopkins Technology Transfer

(57) ABSTRACT

The instant invention provides methods and compositions for the detection of prostate cancer is a subject. In one embodiment, a method of detecting prostate cancer in a subject comprises the steps of (a) detecting the presence of at least one biomarker listed in Table 1 in a serum sample, wherein the presence of the biomarker in the serum sample is indicative of prostate cancer.

5 Claims, 18 Drawing Sheets

Matched fragment ions for native and heavy peptide

| Native peptide: N*KSVILLGR (1000.61) | | | | Heavy peptide: N*#KSVILLGR (1005.61) | | | |
|---|---|---|---|---|---|---|---|
| Centroid Mass | Height | S/N Ratio | Fragment | Centroid M | Height | S/N Ratio | Fragment |
| 175.10 | 65.00 | 66.36 | Y1 | 175.11 | 46.00 | 47.72 | Y1 |
| 232.12 | 27.00 | 28.01 | Y2 | 232.13 | 21.00 | 21.29 | Y2 |
| 244.11 | 14.00 | 14.19 | B2 | 249.13 | 11.00 | 11.24 | B2 |
| 331.14 | 11.00 | 12.38 | B3 | 336.18 | 13.00 | 12.15 | B3 |
| 345.19 | 21.00 | 22.23 | Y3 | 345.22 | 18.00 | 18.23 | Y3 |
| 430.21 | 23.00 | 24.45 | B4 | 435.21 | 22.00 | 22.43 | B4 |
| 458.28 | 23.00 | 24.32 | Y4 | 458.28 | 16.00 | 17.11 | Y4 |
| 543.28 | 16.00 | 16.69 | B5 | 548.31 | 21.00 | 22.30 | B5 |
| 571.38 | 18.00 | 18.85 | Y5 | 571.38 | 15.00 | 16.36 | Y5 |
| 656.38 | 22.00 | 25.45 | B6 | 661.38 | 17.00 | 16.16 | B6 |
| 670.45 | 14.00 | 14.33 | Y6 | 670.45 | 12.00 | 13.27 | Y6 |
| 757.44 | 13.00 | 10.83 | Y7 | 757.48 | 10.00 | 11.90 | Y7 |
| 885.61 | 161.00 | 183.55 | Y8 | 885.64 | 126.00 | 153.17 | Y8 |

FIG. 2E

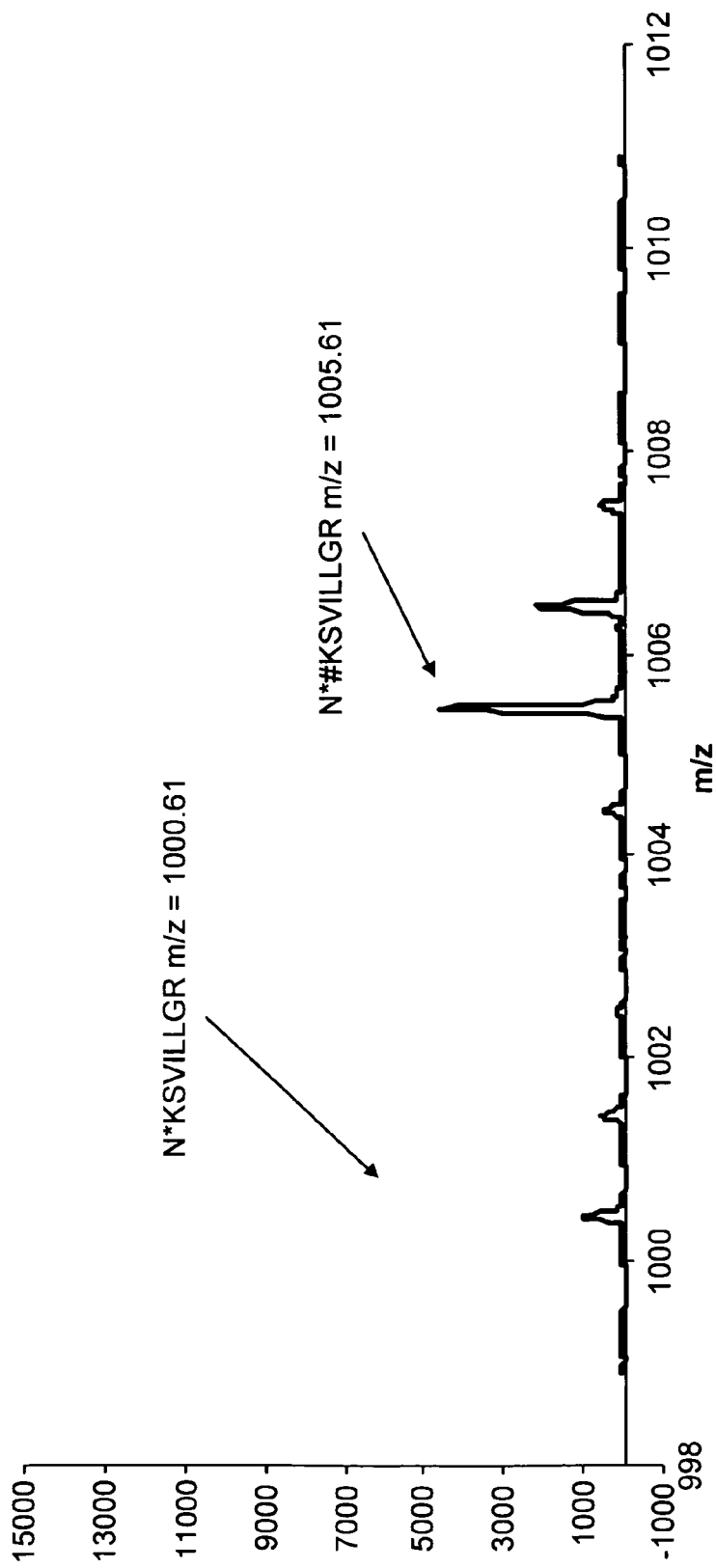
FIG. 2F-a

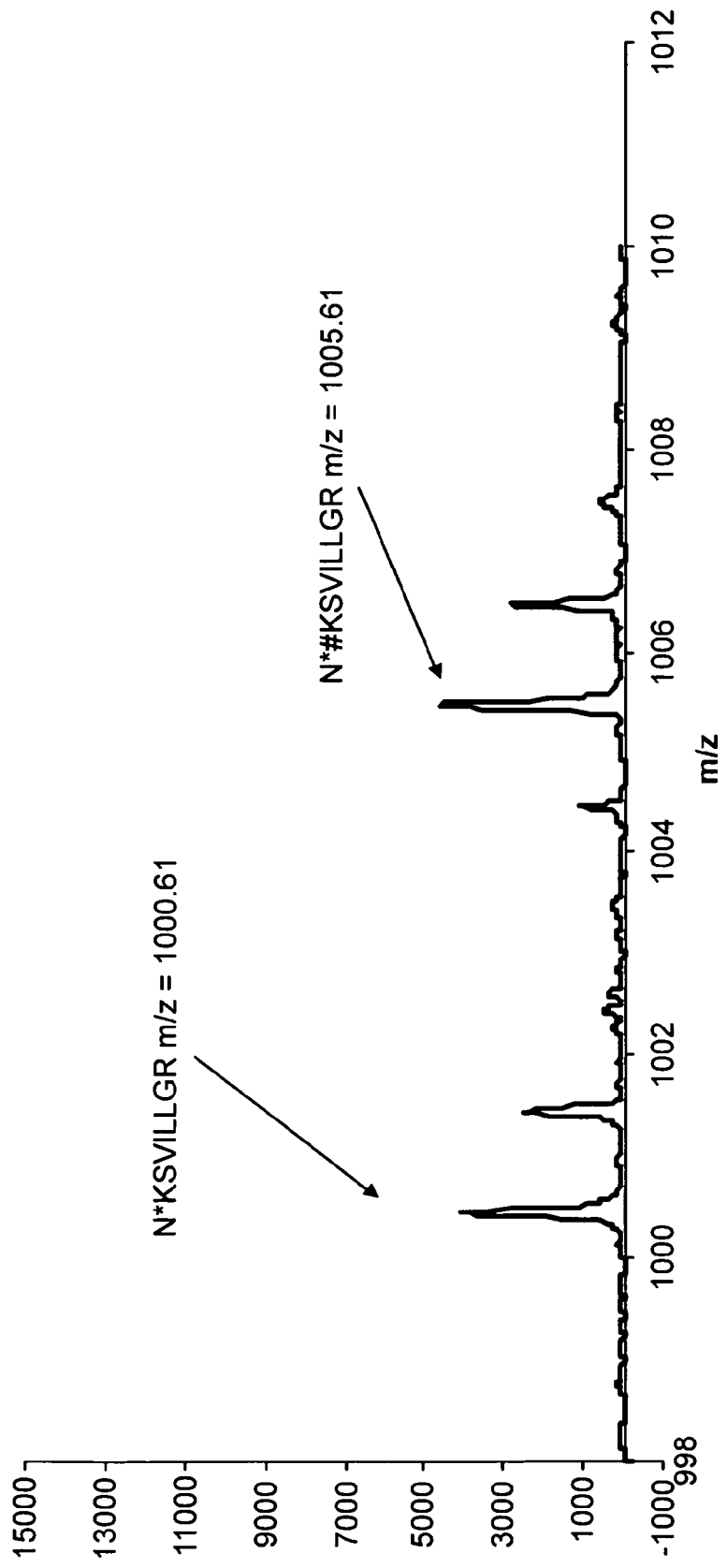
FIG. 2F-b

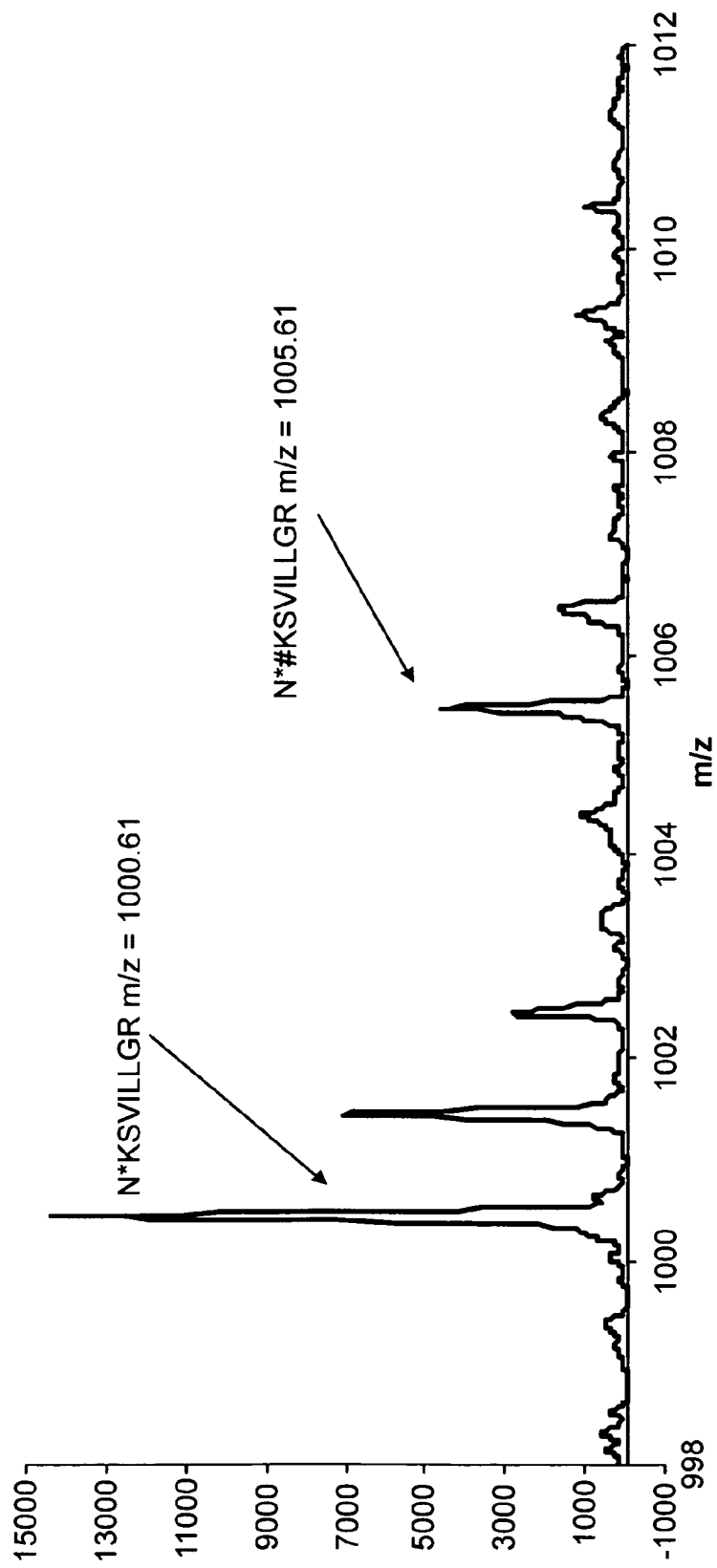
FIG. 2F-c

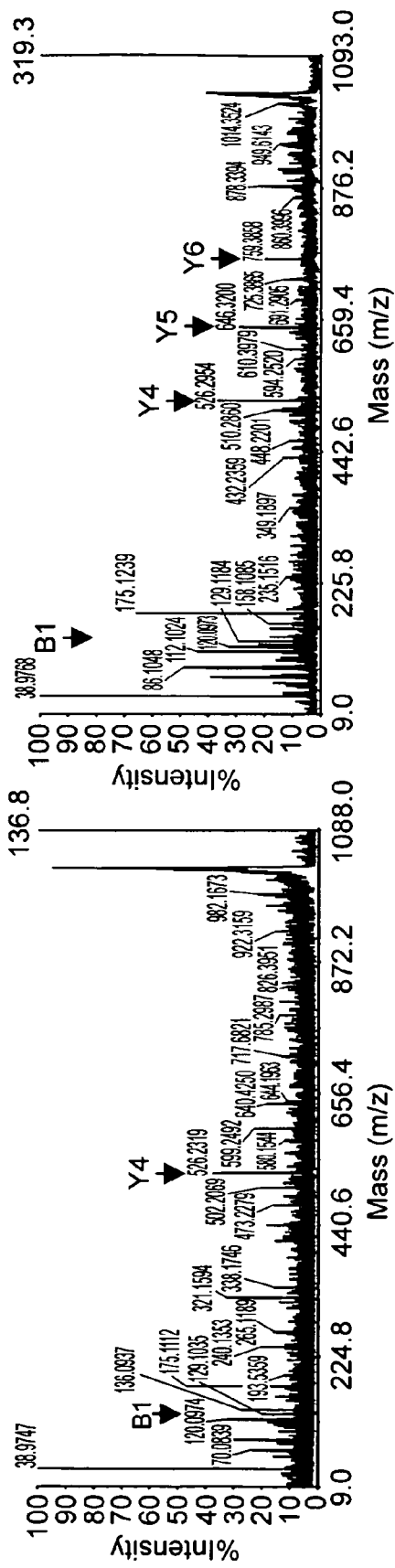

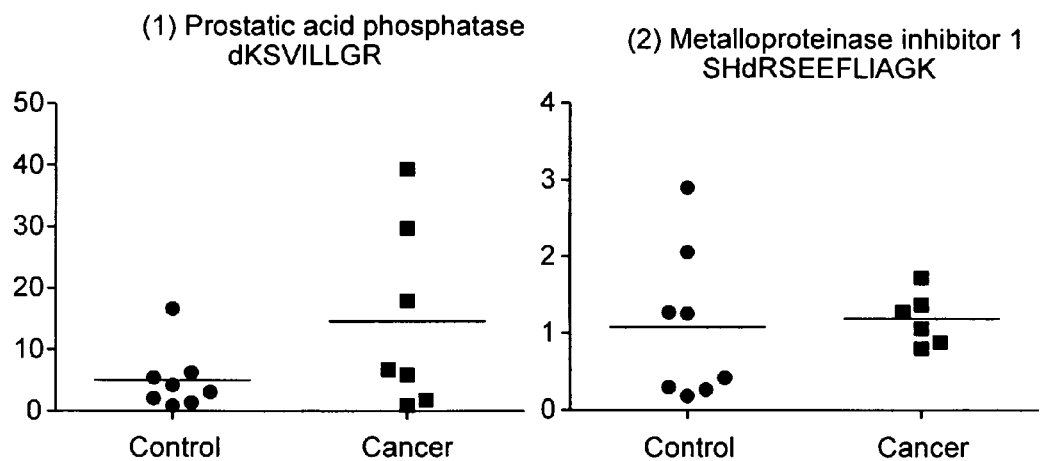
FIG. 4-1
FIG. 4-2
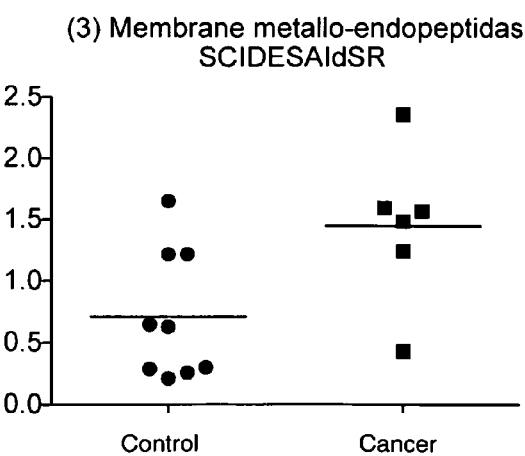
FIG. 4-3

Table 1. The glycoproteins over expressed in prostate cancer tissues and their detection in serum samples. The peptide sequences were selected to synthesize heavy-isotope-labeled-peptide standards in this study.

| Protein Name (gene) | Peptide Sequences | Prostate | Others | mRNA | Serum |
|---|---|---|---|---|---|
| Kallikrein 11 (KLK11) | TATESFPHPGFDNSLPNKdHR (SEQ ID NO:1) | 11 | 0 | 19 | |
| Prostate stem cell antigen (PSCA) | AQVSNEDCLQVEdCTQLGEQCWTAR (SEQ ID NO:2) | 1 | 0 | 26 | |
| Prostate specific antigen (KLK3) | dKSVILLGR (SEQ ID NO:3) | 6 | 0 | 1901 | 1 |
| Prostatic acid phosphatase (ACPP) | KFLdESYK (SEQ ID NO:4) | 93 | 0 | 1885 | 1 |
| Olfactomedin 4 (GW112) | VdLTNTIAVTQTLPNAAYNNR (SEQ ID NO:5) | 3 | 1 | 80 | |
| Metalloproteinase inhibitor 1 (TIMP1) | SHdRSEEFLIAGK (SEQ ID NO:6) | 3 | 2 | 5 | 1 |
| Membrane metallo-endopeptidase (MME) | SCIDESAIdSR (SEQ ID NO:7) | 2 | 1 | 17 | 1 |
| Gamma-glutamyltranspeptidase 1, CD224 (GGT1) | LHNQLLPdVTTVER (SEQ ID NO:8) | 1 | 1 | 26 | 1 |

Prostate: The numbers indicate the frequency of the glycoprotein identifications from prostate tissues in a total of 3997 identifications.
Others: The numbers indicate the frequency of the glycoprotein identifications from 4 tissue and 3 cell types other than prostate tissue with a total of 35638 identifications.
mRNA: Gene expression data from GeneAtlas. The numbers indicate the ratio of the microarray signal of the specific gene from prostate to the median signal of all tissues and cells. A ubiquitous expressed gene will have mRNA ratio of 1 and 4% of genes have ratio over 5.
Serum: Number 1 indicates the glycopeptides from the glycoproteins have been detected in sera from patients with prostate cancer in this study.
d: heavy-isotope-labeled aspartic acid

FIG. 5

SEQUENCE LISTING

```
<160> NUMBER OF SEQ ID NOS: 18

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)
<223> OTHER INFORMATION: Heavy-isotope-labeled Asp

<400> SEQUENCE: 1
```

Thr Ala Thr Glu Ser Phe Pro His Pro Gly Phe Asp Asn Ser Leu Pro
 1               5                  10                  15

Asn Lys Asp His Arg
            20

<210> SEQ ID NO 2
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: Heavy-isotope-labeled Asp

<400> SEQUENCE: 2

Ala Gln Val Ser Asn Glu Asp Cys Leu Gln Val Glu Asp Cys Thr Gln
 1               5                  10                  15

Leu Gly Glu Gln Cys Trp Thr Ala Arg
            20                  25

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Heavy-isotope-labeled Asp

<400> SEQUENCE: 3

Asp Lys Ser Val Ile Leu Leu Gly Arg
 1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Heavy-isotope-labeled Asp

<400> SEQUENCE: 4

Lys Phe Leu Asp Glu Ser Tyr Lys
 1               5

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Heavy-isotope-labeled Asp

<400> SEQUENCE: 5

Val Asp Leu Thr Thr Asn Thr Ile Ala Val Thr Gln Thr Leu Pro Asn

```
                1               5                  10                  15
Ala Ala Tyr Asn Asn Arg
            20

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Heavy-isotope-labeled Asp

<400> SEQUENCE: 6

Ser His Asp Arg Ser Glu Glu Phe Leu Ile Ala Gly Lys
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Heavy-isotope-labeled Asp

<400> SEQUENCE: 7

Ser Cys Ile Asp Glu Ser Ala Ile Asp Ser Arg
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Heavy-isotope-labeled Asp

<400> SEQUENCE: 8

Leu His Asn Gln Leu Leu Pro Asp Val Thr Thr Val Glu Arg
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Asn or heavy-isotope-labeled Asp
<220> FEATURE:
<223> OTHER INFORMATION: See specification as filed for detailed
      description of substitutions and preferred embodiments

<400> SEQUENCE: 9

Xaa Lys Ser Val Ile Leu Leu Gly Arg
1               5
```

```
<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Asn or Asp
<220> FEATURE:
<223> OTHER INFORMATION: See specification as filed for detailed
      description of substitutions and preferred embodiments

<400> SEQUENCE: 10

Xaa Lys Ser Val Ile Leu Leu Gly Arg
 1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Asn or Asp
<220> FEATURE:
<223> OTHER INFORMATION: See specification as filed for detailed
      description of substitutions and preferred embodiments

<400> SEQUENCE: 11

Lys Phe Leu Xaa Glu Ser Tyr Lys
 1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Asn or heavy-isotope-labeled Asp
<220> FEATURE:
<223> OTHER INFORMATION: See specification as filed for detailed
      description of substitutions and preferred embodiments

<400> SEQUENCE: 12

Lys Phe Leu Xaa Glu Ser Tyr Lys
 1               5

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Asn or Asp
<220> FEATURE:
<223> OTHER INFORMATION: See specification as filed for detailed
      description of substitutions and preferred embodiments

<400> SEQUENCE: 13
```

```
Ser His Xaa Arg Ser Phe Phe Glu Leu Ile Ala Gly Lys
 1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Asn or heavy-isotope-labeled Asp
<220> FEATURE:
<223> OTHER INFORMATION: See specification as filed for detailed
      description of substitutions and preferred embodiments

<400> SEQUENCE: 14

Ser His Xaa Arg Ser Phe Phe Glu Leu Ile Ala Gly Lys
 1               5                   10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Asn or heavy-isotope-labeled Asp
<220> FEATURE:
<223> OTHER INFORMATION: See specification as filed for detailed
      description of substitutions and preferred embodiments

<400> SEQUENCE: 15

Ser Cys Ile Asp Glu Ser Ala Ile Xaa Ser Arg
 1               5                   10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Asn or Asp
<220> FEATURE:
<223> OTHER INFORMATION: See specification as filed for detailed
      description of substitutions and preferred embodiments

<400> SEQUENCE: 16

Ser Cys Ile Asp Glu Ser Ala Ile Xaa Ser Arg
 1               5                   10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Asn or Asp
<220> FEATURE:
```

-continued

```
<223> OTHER INFORMATION: See specification as filed for detailed
      description of substitutions and preferred embodiments

<400> SEQUENCE: 17

Leu His Asn Gln Leu Leu Pro Xaa Val Thr Thr Val Glu Arg
  1               5                  10

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Asn or heavy-isotope-labeled Asp
<220> FEATURE:
<223> OTHER INFORMATION: See specification as filed for detailed
      description of substitutions and preferred embodiments

<400> SEQUENCE: 18

Leu His Asn Gln Leu Leu Pro Xaa Val Thr Thr Val Glu Arg
  1               5                  10
```

BIOMARKERS FOR PROSTATE CANCER

GOVERNMENT SUPPORT

The following invention was supported, at least in part, by the National Institutes of Health, grant R21-CA-114852. Accordingly, the government has certain rights in the invention.

RELATED APPLICATIONS

This application is a 35 U.S.C. §371 U.S. national entry of International Application PCT/US2008/065782 (WO 2008/151238) and claims the benefit of U.S. Provisional Application No. 60/933,020, filed Jun. 4, 2007, the entire contents of which applications are incorporated herein by reference.

BACKGROUND OF THE INVENTION

Cancers develop over a period of several years and are characterized by molecular changes in cancer cells or tissue prior to noticeable symptoms (1). If such changes in tumor tissues can be detected in a patient's serum or blood, they can be used as biomarkers that could have a significant impact on clinical outcomes.

Within the past decade, advances in proteomic technologies have stimulated a search for serum biomarkers by profiling serum proteomic patterns (2,3). However, when these discriminatory proteins are identified, they have often turned out to be well-known high abundant classical plasma proteins or acute-phase proteins (6). Although these high abundant plasma proteins are indicators of interesting biology and have been shown to associate with different types of cancer (7), they are not likely derived from tumor tissue as specific tumor markers. Instead, useful serum biomarkers for tumor detection are those proteins released in small amounts specifically from tumors, indicated a specific response of the system to cancer cells, or entered to blood due to structural changes in the microenvironment surrounding cancer cells (8).

Ideally, if proteins from specific tumors can be detected in patients' blood and the abundance of these proteins in blood is associated with tumor development, these proteins can be used as candidate targets to develop assays for the detection of cancer in the specific tissue using blood tests.

Since the discovery of prostate-specific antigen (PSA), PSA as serum biomarker has been developed as the best serum marker for the early detection of cancer. The screening of prostate cancer using the PSA test has resulted in early intervention with effective treatments and decreased morbidity (13,14). PSA has specific expression in prostate with leakage to patients' blood during cancer development. However, PSA measurement has limitations, since the test is not specific for prostate cancer. PSA can also be elevated due to benign prostate diseases such as benign prostatic hyperplasia and prostatitis. The 4-10 ng/mL PSA range has been termed the "diagnostic gray zone" due to such overlap in PSA concentrations. Several studies have shown that a significant incidence of cancer (24.5%) occurs in men with total serum PSA concentrations between 2.5-4.0 ng/ml range, similar to the 4-10 ng/mL range (15), although it has also been recognized that prostate cancer can occur over all PSA ranges (16, 17).

Therefore, the need exists for new biomarkers that will increase the accuracy of prostate cancer detection.

SUMMARY OF THE INVENTION

The instant invention is based, at least in part, on the inventors discovery of prostate cancer biomarkers. In one embodiment, the biomarkers are serum biomarkers for prostate cancer.

Accordingly, in one aspect, the instant invention provides methods of detecting prostate cancer in a subject, by detecting the presence of at least one biomarker listed in Table 1 in a serum sample, wherein the presence of the biomarker in the sample is indicative of prostate cancer. The biomarkers listed in table 1 are: olfactomedin 4 (GW112), gamma-glutamyl-transpeptidase 1 (GGT1), prostate stem cell antigen (PSCA), membrane metallo-endopeptidase (MME), prostate specific antigen (KLK3), prostatic acid phosphatase (ACPP), metalloproteinase inhibitor 1(TIMP1), and Kallikrein 11 (KLK11).

In one embodiment, the methods further comprise determining the amount of biomarker in the sample. In another embodiment, the methods further comprise measuring the amount of an additional biomarker, e.g., PSA. In one embodiment, the methods of the invention are used to determine the presence or absence of cancer in subjects who have PSA levels of 10 ng/ml or less.

In one embodiment, the methods comprise detecting the presence of the biomarker polypeptide by, for example, mass spectrometry, immunohistochemistry, ELISA, lectin, or gel electrophoresis. In another embodiment, the methods comprise detecting the presence of the mRNA encoding the biomarker polypeptide. In related embodiments, the methods further comprise determining the amount of the biomarker polypeptide or nucleic acid, i.e., mRNA, in a sample.

In one particular embodiment, the methods of detecting the presence or measuring the level of the at least one biomarker comprises the steps of: contacting a sample with an antibody or antibodies which selectively bind the one or more biomarkers; and detecting whether the antibody or antibodies is bound by the sample and thereby detecting the presence of or measuring the levels of the at least one biomarker. In a related embodiment, the antibody or antibodies are detectably labeled.

In another aspect, the invention provides methods of detecting prostate cancer in a subject, by detecting the presence of gamma-glutamyltranspeptidase 1 (GGT1) in a serum sample, wherein the presence of GGT1 in the sample is indicative of prostate cancer.

In one embodiment, the methods comprise detecting the presence of GGT1 polypeptide by, for example, mass spectrometry, immunohistochemistry, ELISA, lectin, or gel electrophoresis. In another embodiment, the methods further comprise determining the amount of GGT1 polypeptide in the sample. In another embodiment, the subject has a PSA level of 10 ng/ml or less.

In another aspect, the invention provides methods of detecting cancer in a subject, by detecting the presence of membrane metallo endopeptidase (MME) in a serum sample, wherein the presence of MME in the sample is indicative of prostate cancer.

In one embodiment, the methods comprise detecting the presence of MME polypeptide by, for example, mass spectrometry, immunohistochemistry, ELISA, lectin, or gel electrophoresis. In another embodiment, the methods further comprise determining the amount of MME polypeptide in the sample. In another embodiment, the subject has a PSA level of 10 ng/ml or less.

In another aspect, the invention provides methods for the early detection of prostate cancer in a subject by detecting the presence of MME or GGT1 polypeptide in a serum sample from a subject having PSA levels of 10 ng/ml or less, thereby detecting the prostate cancer in the subject. In one embodiment, the invention further comprises obtaining the serum sample from a subject.

In another embodiment, the subject is preselected as having an increased likelihood of having cancer.

In another embodiment, the presence of both MME and GGT1 are identified. In a related embodiment, the methods further comprise determining the amount of MME or GGT1 in the sample.

In another aspect, the invention provides kits for detecting the presence or amount of one or more biomarkers in Table 1 in a sample comprising antibodies, or antibody fragments, which selectively bind to the biomarkers, and instructions for use.

In another aspect, the invention provides kits for detecting one or more biomarkers in Table 1 in a sample comprising isotopically labeled peptides corresponding to on one or more peptides derived from one or more polypeptide set forth in Table 1, and instructions for use.

In another aspect, the invention provides kits for detecting the presence or amount of MME in a sample comprising an antibody, or antibody fragment, which selectively binds to MME, and instructions for use.

In another aspect, the invention provides kits for detecting the presence or amount of MME in a sample comprising isotopically labeled peptides corresponding to one or more peptides derived from MME, and instructions for use. In one embodiment, the peptide comprises the sequence SCIDESAIdSR (SEQ ID NO: 7), wherein d indicates a heavy isotope labeled aspartic acid.

In another aspect, the invention provides kits for detecting the presence or amount of GGT1 in a sample comprising an antibody, or antibody fragment, which selectively binds to GGT1, and instructions for use.

In another aspect, the invention provides kits for detecting the presence or amount of GGT1 in a sample comprising isotopically labeled peptides corresponding to peptides derived from GGT1, and instructions for use. In one embodiment, the peptide comprises the sequence LHNQLLPdVTTVER (SEQ ID NO: 8), wherein d indicates a heavy isotope labeled aspartic acid.

DESCRIPTION OF THE DRAWINGS

FIG. 5 depicts Table 1 setting forth the biomarkers of the invention. The glycoproteins set forth in the table are over expressed in prostate cancer tissues and the peptide sequences set forth in Table 1 were selected to synthesize heavy-isotope-labeled-peptide standards. Five of these glycoproteins have been detected in serum samples.

DETAILED DESCRIPTION OF THE INVENTION

Figure 1:
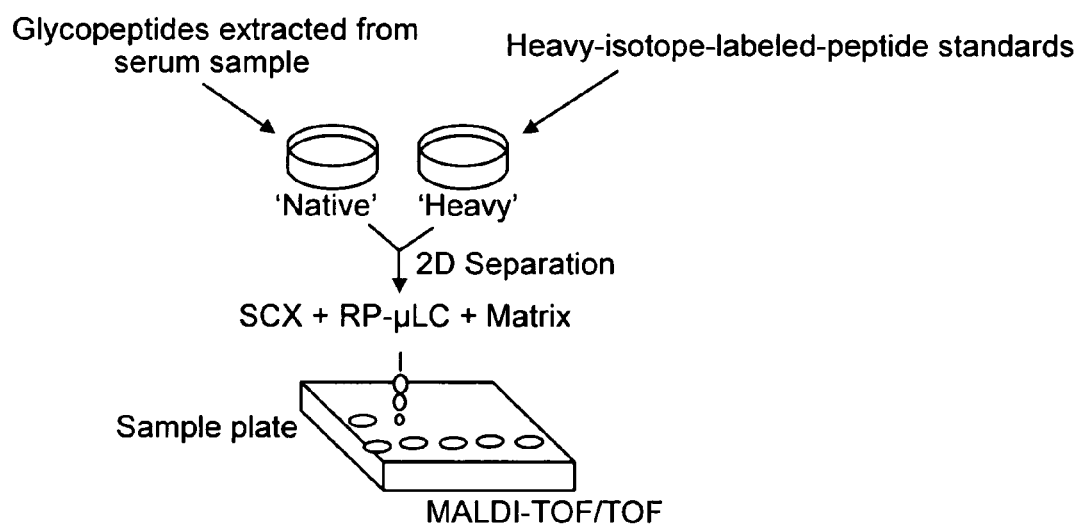
FIG. 1: Schematic diagram of detection of glycopeptides identified from prostate cancer tissues in patients' sera using heavy-isotope-labeled-peptide standards and a 2D-LC-MALDI-TOF/TOF-MS platform.
Figure 2A:
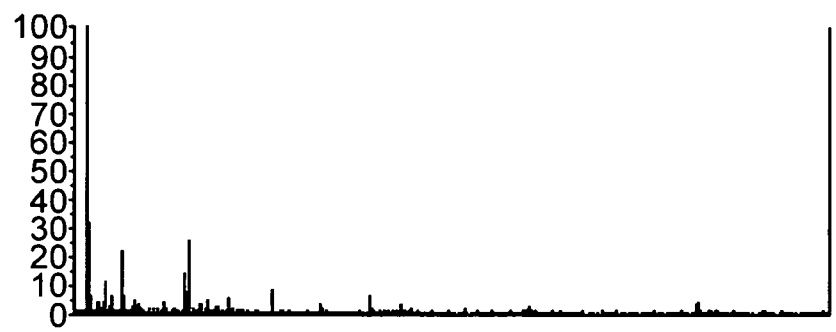
FIG. 2: Prostate-specific antigen (PSA) sensitivity test. PSA concentration was 10 ng/ml in serum sample. A) The native peptide was initially paired with the heavy-isotope-labeled-peptide standards on same spot to identify the native peptide. B) An enlargement of the peptide pairs from MS spectra with native peptide sequence N*KSVILLGR (m/z=1000.61) (SEQ ID NO:10) and heavy peptide sequence N*#KSVILLGR (m/z=1005.61) (SEQ ID NO:9). C) and D) MS/MS spectra of native peptide (N*KSVILLGR m/z=1000.61) (SEQ ID NO:10) and heavy-isotope-labeled peptide (N*#KSVILLGR m/z=1005.61) (SEQ ID NO:9) were used to confirm the peptide sequence. Detected y ions were labeled on both spectra. E) The list of matched fragment ions for native (SEQ ID NO:10) and heavy peptides (SEQ ID NO:9). F) The MS1 spectra of prostate-specific antigen (PSA) sensitivity test. The native peptide spike-in amount with clinical assay measurement is (a) 3.44 ng/ml, (b) 9.95 ng/ml and (c) 51.43 ng/ml in pooled healthy woman serum. Spectra were normalized by heavy peptide (SEQ ID NO:9) peak height. (N*:N-linked glycosylation site and was converted to D after deglycosylation). (#: heavy-isotope-labeling aspartic acid). G) The calibration curve for detection sensitivity of PSA detection from pooled serum from healthy women. The native to heavy ratio was calculated by mono-isotopic peak area. (N*:N-linked glycosylation site and was converted to D after deglycosylation). (#: heavy-isotope-labeling aspartic acid)
Figure 2B:
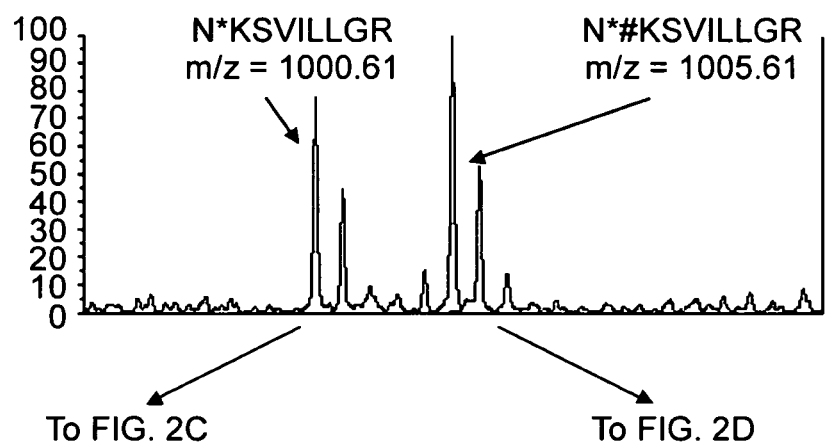
Figure 2D:
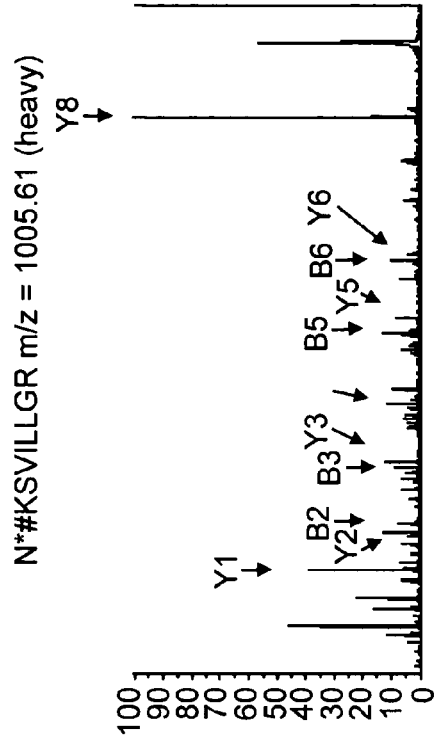
Figure 2C:
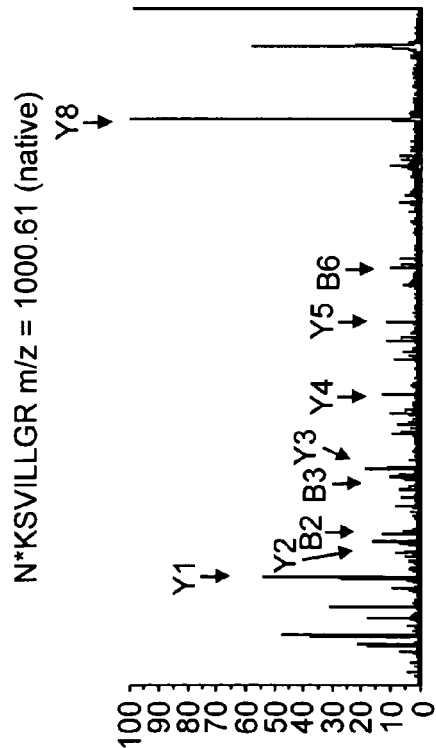
Figure 2G:
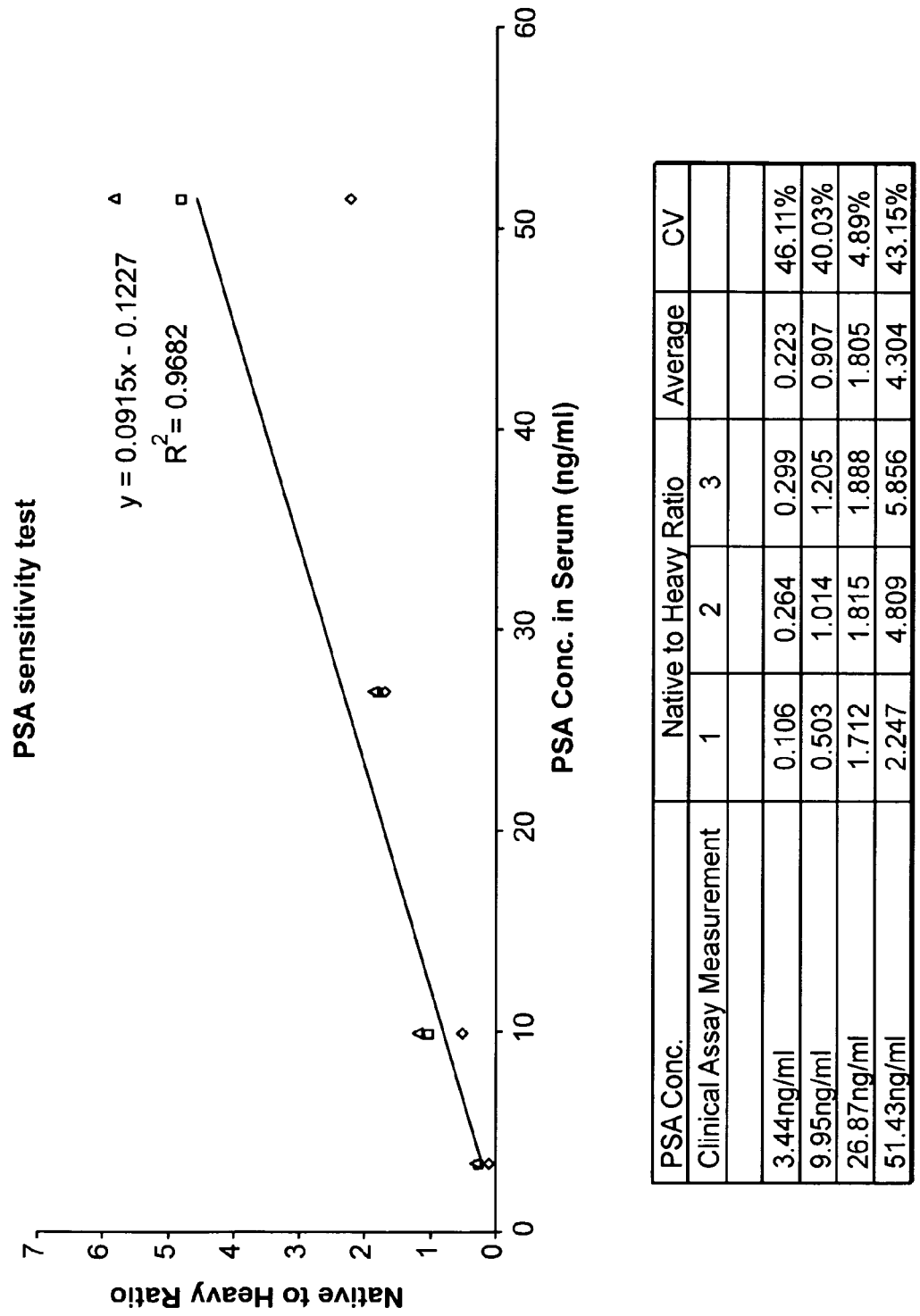

The term "biomarker" refers to a molecule that is produced by a cell or tissue in an organism. Such molecules include, but are not limited to, molecules such as nucleic acids, nucleotides, oligonucleotides, polynucleotides, amino acids, peptides, polypeptides, proteins, monoclonal and/or polyclonal antibodies, antigens, sugars, carbohydrates, fatty acids, lipids, steroids, and combinations thereof (e.g., glycoproteins, ribonucleoproteins, lipoproteins). Furthermore, the terms "nucleotide", "oligonucleotide" or polynucleotide" refer to DNA or RNA of genomic or synthetic origin which may be single-stranded or double-stranded and may represent a sense or an antisense strand. Included as part of the definition of "oligonucleotide" and "polynucleotide" are peptide polynucleotide sequences (i.e. peptide nucleic acids; PNAs), or any DNA-like or RNA-like material (i.e. Morpholinos, Ribozymes). In a preferred embodiment of the invention, biomarkers are polypeptides expressed by cancerous cells, e.g., prostate cancer cells. In specific examples, the biomarkers of the invention are those set froth in Table 1.

Table 1 sets forth eight biomarkers of the invention. Specifically, Table 1 sets forth olfactomedin 4 (GW112), gamma-glutamyltranspeptidase 1 (GGT1), prostate stem cell antigen (PSCA), membrane metallo-endopeptidase (MME), prostate specific antigen (KLK3), prostatic acid phosphatase (ACPP), metalloproteinase inhibitor 1 (TIMP1), and Kallikrein 11 (KLK11). The gene encoding each biomarker is set forth in parenthesis after the name of each biomarker.

The sequences of the biomarkers of the invention are known in the art and can be found in publicly available publications and databases. Exemplary sequences are set froth below in the form of GenBank accession numbers. The nucleic acid and polypeptide accession numbers, respectively, are set forth in parenthesis after each biomarker; olfactomedin 4 (NM_006418; NP_006409), gamma-glutamyl-transpeptidase 1 (NM_005265; NP_005256), prostate stem cell antigen (NM_005672; NP_005663), membrane metallo-endopeptidase (NM_000902; NP_00893), prostate specific antigen (NM_001648; NP_001639), prostatic acid phosphatase (NM_001099; NP_001090), metalloproteinase inhibitor 1 (NM_003254; NP_03245), and Kallikrein 11 (NM_AAQ89373; NP_AY359014). One of skill in the art will understand that although accession numbers are provided, each biomarker may exist in multiple forms. For example, variants may exist in which a small number, e.g., 1, 2, 3, 4, 5, 10 or more, nucleotides or amino acid residues are different that the exemplary accession numbers set forth above. However, these variants are intended to be used in the methods of the invention. The biomarkers are further set forth in Table 1.

modified form of a given biomarker may include at least one amino acid substitution, deletion, or insertion, wherein said modified form retains a biological activity of an unmodified form. An amino acid substitution may be considered "conservative" when the substitution results in similar structural or chemical properties (e.g., replacement of leucine with isoleucine). An amino acid substitution may be "non-conservative" in nature wherein the structure and chemical properties vary (e.g., replacement of arginine with alanine). A modified form of a given biomarker may include chemical modifications, wherein a modified form retains a biological activity of a given biomarker. Such modifications include, but are not limited to, glycosylation, phosphorylation, acetylation, alkylation, methylation, biotinylation, glutamylation glycylation, isoprenylation, lipoylation, pegylation, phosphopantetheinylation, sulfation, selenation, and C-terminal amidation. Other modifications include those involving other proteins such as ISGylation, SUMOylation, and ubiquitination. In addition, modifications may also include those involved in changing the chemical nature of an amino acid such as deimination and deamidation.

The phrases "biological sample" and "test sample" refer to all biological fluids and excretions isolated from any given subject. In the context of the invention such samples include, but are not limited to, blood, serum, plasma, urine, semen, seminal fluid, seminal plasma, pre-ejaculatory fluid (Cowper's fluid), nipple aspirate, vaginal fluid, excreta, tears, saliva, sweat, biopsy, ascites, cerebrospinal fluid, lymph, marrow, hair, or tissue extract samples. In a preferred embodiment of the inveitons, the biological sample is a serum sample.

TABLE 1

| Protein Name (gene) | Peptide Sequences | Prostate | Others | mRNA | Serum |
|---|---|---|---|---|---|
| Kallikrein 11 (KLK11) | TATESFPHPGFDNSLPNKdHR (SEQ ID NO: 1) | 11 | 0 | 19 | |
| Prostate stem cell antigen (PSCA) | AQVSNEDCLQVEdCTQLGEQCWTAR (SEQ ID NO: 2) | 1 | 0 | 26 | |
| Prostate specific antigen (KLK3) | dKSVILLGR (SEQ ID NO: 3) | 6 | 0 | 1901 | 1 |
| Prostatic acid phosphatase (ACPP) | KFLdESYK (SEQ ID NO: 4) | 93 | 0 | 1885 | 1 |
| Olfactomedin 4 (GW112) | VdLTTNTIAVTQTLPNAAYNNR (SEQ ID NO: 5) | 3 | 1 | 80 | |
| Metalloproteinase inhibitor 1 (TIMP1) | SHdRSEEFLIAGK (SEQ ID NO: 6) | 3 | 2 | 5 | 1 |
| Membrane metallo-endopeptidase (MME) | SCIDESAIdSR (SEQ ID NO: 7) | 2 | 1 | 17 | 1 |
| Gamma-glutamyltranspeptidase 1, CD224 (GGT1) | LHNQLLPdVTTVER (SEQ ID NO: 8) | 1 | 1 | 26 | 1 |

The term "fragment" refers to a portion of a polynucleotide or polypeptide sequence that comprises at least 15 consecutive nucleotides or 5 consecutive amino acid residues, respectively. Furthermore, these "fragments" typically retain the biological activity and/or some functional and structural characteristics of the parent polypeptide e.g. antigenicity or structural domain characteristics.

The term "derivative" refers to a modified form of a biomarker and can include biomarkers set forth in Table 1. A The term "host cell" refers to a cell that has been transformed or transfected, or is capable of transformation or transfection by an exogenous polynucleotide sequence. It is understood that such terms refer not only to a particular subject cell but also to a progeny or potential progeny of such a cell. Since certain modifications may occur in succeeding generations due to either mutation or environmental influences, such progeny may not, in fact, be identical to the parent cell, but are still included within the scope of the term as used herein. A host cell can be a cancer cell.

The phrase "specific binding" refers to an interaction between two biomolecules that occur under specific conditions. The binding is specific when one biomolecule adheres to a specific biomolecule and not other biomolecules. Binding between two biomolecules is considered to be specific when the signal of the peak representing the biomolecule is at least twice that of the signal arising from the coincidental detection of non-biomolecule associated ions in approximately the same mass range, which is the peak as a signal to noise ratio of at least two. Moreover, the phrase "specific conditions" refers to reaction conditions that permit, enable, or facilitate the binding of said molecules such as pH, salt, detergent and other conditions known to those skilled in the art.

The term "interaction" refers to direct or indirect binding or alteration of a biological activity of a biomolecule, e.g., a biomarker.

The term "differential diagnosis" refers to a diagnostic decision between healthy and different disease states, including various stages of a specific disease. A subject is diagnosed as healthy or to be suffering from a specific disease, or a specific stage of a disease based on a set of hypotheses that allow for a distinction between healthy and one or more stages of the disease. A choice between healthy and one or more stages of disease depends on a significant difference between each hypothesis. Under the same principle, a "differential diagnosis" may also refer to a diagnostic decision between one disease type as compared to another. In a specific embodiment, a differential diagnosis of the invention is between the presence of prostate cancer and the absence of prostate cancer.

The term "prostate cancer" refers to a neoplasm, e.g., malignant neoplasm, of the prostate within a given subject, wherein the neoplasm is of epithelial origin. The term "prostate cancer", when used without qualification, includes both localized and metastasized prostate cancer. The term "prostate cancer" can be qualified by the terms "localized" or "metastasized" to differentiate between different types of tumor as those words are defined herein.

The term "stage of prostate cancer" as used herein can be defined by one of a number of accepted systems for classifying the progression of prostate cancer. For example, the Jewett-Whitmore system classifies prostate cancer first as stage A, B, C, or D. Stages A and B cancers are considered curable. Stages C and D are treatable, but their prognoses are discouraging. A number is then assigned to describe specific conditions within each stage. For example, a tumor classified as stage B1 is a single cancerous nodule confined to one lobe of the prostate. More specifically, the stages are defines as follows: Stage A is very early and without symptoms; cancer cells confined to the prostate; Stage A1 is well differentiated and slightly abnormal cancer cells; stage A2 is moderately or poorly differentiated and abnormal cancer cells in several locations within the prostate; stage B is confined to the prostate, but palpable (detectable by digital rectal exam) and/or detectable by elevated PSA; stage B0 is confined to the prostate, nonpalpable; PSA elevated; stage B1 is a single cancerous nodule in one lobe of the prostate; stage B2 is extensive, involvement in one or both prostate lobes. Stage C is cancer cells found outside the prostate capsule (membrane covering the prostate); spread confined to surrounding tissues and/or seminal vesicles; stage C1 extends outside the prostate capsule; and stage C2 has bladder or urethral obstruction. Stage D has metastasis (spread) to regional lymph nodes, or to distant bones, organs (e.g., liver, lungs), and/or other tissues; stage D0 is metastatic, clinically localized, and showing elevated blood PAP levels; stage D1 has regional lymph nodes involved; stage D2 has distant lymph nodes, bones, or organs involve; and stage D3 has metastatic disease after treatment.

Alternatively, the TNM System may be used to stage prostate cancer. The TNM (tumor, node, metastases) system stages are similar to those of the Jewett-Whitmore system, but with more specific alphanumeric subcategories. Stages of prostate cancer according to the TNM system are Primary tumor (T), TX: tumor cannot be assessed; T0: no evidence of primary tumor; T1: clinically not palpable or visible by imaging; T1a: found incidental to other surgery; present in 5% or less of tissue; T1b: found incidental to other surgery; present in 5% or more of tissue; T1c: identified by needle biopsy; T2: tumor confined within prostate; T2a: involving half a lobe or less of prostate; T2b: involving half a lobe; T2c: involving both lobes; T3: tumor extends through prostate capsule; T3a: extends through one lobe; T3b: extends through both lobes; T3c extends into seminal vesicles; T4: involves structures other than seminal vesicles; T4a: invades bladder neck, external sphincter, or rectum; and T4b: invades muscles and/or pelvic wall. Regional Lymph Nodes (N); NX: Nodes cannot be assessed; N0: no regional node metastasis; N1: single node metastasis, 2 centimeters (cm) or less at largest point; N2: single node metastasis, 2 cm to 5 cm at largest point, or multiple nodes, no larger than 5 cm at largest point; N3: metastasis larger than 5 cm in any node; Distant Metastasis (M): MX: metastasis cannot be assessed; M0: no distant metastasis; M1: distant metastasis: M1a: distant lymph node(s) involved; M1b: bone(s) involved; M1c: other site(s) involved.

The terms "neoplasm" or "tumor" may be used interchangeably and refer to an abnormal mass of tissue wherein the growth of the mass surpasses and is not coordinated with the growth of normal tissue. A neoplasm or tumor may be defined as "benign" or "malignant" depending on the following characteristics: degree of cellular differentiation including morphology and functionality, rate of growth, local invasion and metastasis. A "benign" neoplasm is generally well differentiated, has characteristically slower growth than a malignant neoplasm and remains localized to the site of origin. In addition a benign neoplasm does not have the capacity to infiltrate, invade or metastasize to distant sites. A "malignant" neoplasm is generally poorly differentiated (anaplasia), has characteristically rapid growth accompanied by progressive infiltration, invasion, and destruction of the surrounding tissue. Furthermore, a malignant neoplasm has the capacity to metastasize to distant sites.

The term "metastasis" refers to the spread or migration of cancerous cells from a primary (original) tumor to another organ or tissue, and is typically identifiable by the presence of a "secondary tumor" or "secondary cell mass" of the tissue type of the primary (original) tumour and not of that of the organ or tissue in which the secondary (metastatic) tumour is located. For example, a prostate cancer that has migrated to bone is said to be metastasized prostate cancer, and consists of cancerous prostate cancer cells in the large intestine as well as cancerous prostate cancer cells growing in bone tissue.

The phrase "healthy" refers to a subject possessing good health. Such a subject demonstrates an absence of any malignant or non-malignant disease of the prostate. In the context of this application, a "healthy individual" is only healthy in that they have an absence of any malignant or non-malignant disease of the prostate; a "healthy individual" may have other diseases or conditions that would normally not be considered "healthy".

The phrase "neoplastic transformation of a cell" refers an alteration in normal cell physiology and includes, but is not limited to, self-sufficiency in growth signals, insensitivity to growth-inhibitory (anti-growth) signals, evasion of programmed cell death (apoptosis), limitless replicative potential, sustained angiogenesis, and tissue invasion and metastasis.

The phrase "differentially present" refers to differences in the quantity of a biomarker present in samples taken from prostate cancer patients as compared to samples taken from healthy subjects, i.e., subjects who do not have prostate cancer. Furthermore, a biomarker is differentially present between two samples if the quantity of said biomarker in one sample population is significantly different (defined statistically) from the quantity of said biomarker in another sample population. For example, a given biomarker may be present at elevated, decreased, or absent levels in samples of taken from subjects having prostate cancer compared to those taken from subjects who do not have a prostate cancer. In specific embodiments, the biomarkers of Table 1 are differentially present in prostate cancer subjects, e.g., they are expressed in subjects having prostate caner, but not expressed in subject who do not have prostate cancer.

The terms 'neoplastic cell' and 'neoplastic tissue' refer to a cell or tissue, respectively, that has undergone transformation, which is manifested by an escape from specific control mechanisms, increased growth potential, alteration in the cell surface, karyotypic abnormalities, morphological and biochemical deviations from the norm, and other attributes conferring the ability to invade, metastasize and kill The term "diagnostic assay" can be used interchangeably with "diagnostic method" and refers to the detection of the presence or nature of a pathologic condition. Diagnostic assays differ in their sensitivity and specificity, and their relative usefulness as a diagnostic tool can be measured using statistics.

The term "diagnostic gray zone" refers to subjects who fall in the range of PSA scores wherein it is often difficult to determine if the subject has prostate cancer. Specifically, subjects with PSA scores from 2-15, or more commonly 4-10 fall in a zone wherein measuring the PSA levels is not indicative of the presence of absence of disease. The subjects falling within this gray zone are often falsely diagnosed as having or not having cancer. Subjects falling within this gray zone will benefit from the methods provided herein.

Within the context of the invention, the term "true positives" refers to those subjects having a localized or a metastasized prostate cancer.

Within the context of the invention, the term "false negatives" refers to those subjects having either a localized or a metastasized prostate cancer and are not categorized as such by a diagnostic assay.

Within the context of the invention, the term "true negatives" refers to those subjects who do not have a localized or a metastasized prostate cancer and who are categorized as such by a diagnostic assay.

Within the context of the invention, the term "false positives" refers to those subjects who do not have a localized or a metastasized prostate cancer but are categorized by a conventional diagnostic assay as having a localized or metastasized prostate cancer. Depending on context, the term "false positives" may also refer to those subjects who do not have prostate cancer but are categorized by a diagnostic assay as having prostate cancer or a non-malignant disease of the large intestine.

The term "sensitivity", as used herein in the context of its application to diagnostic assays, refers to the proportion of all subjects with localized or metastasised prostate cancer that are correctly identified as such (that is, the number of true positives divided by the sum of the number of true positives and false negatives).

The term "specificity" of a diagnostic assay, as used herein in the context of its application to diagnostic assays, refers to the proportion of all subjects with neither localized or metastasized prostate cancer that are correctly identified as such (that is, the number of true negatives divided by the sum of the number of true negatives and false positives).

The term "adsorbent" refers to any material that is capable of accumulating (binding) a given biomarker. The adsorbent typically coats a biologically active surface and comprises a single material or a plurality of different materials that are capable of binding a biomarker. Such materials include, but are not limited to, anion exchange materials, cation exchange materials, metal chelators, polynucleotides, oligonucleotides, peptides, antibodies, naturally occurring compounds, synthetic compounds, etc.

The phrase "biologically active surface" refers to any two- or three-dimensional extensions of a material that biomolecules can bind to, or interact with, due to the specific biochemical properties of this material and those of the biomolecules. Such biochemical properties include, but are not limited to, ionic character (charge), hydrophobicity, or hydrophilicity.

The term "chromatography" refers to a method of separating biomolecules within a given sample so as to enrich the population for biomarkers, such that an original native state of a given biomolecule is retained. Separation of a biomolecule from other biomolecules within a given sample for the purpose of enrichment, purification an or analysis may be achieved by methods including, but not limited to, size exclusion chromatography, ion exchange chromatography, hydrophobic and hydrophilic interaction chromatography, metal affinity chromatography, wherein "metal" refers to metal ions (e.g. nickel, copper, gallium, zinc, iron or cobalt) of all chemically possible valences, or ligand affinity chromatography wherein "ligand" refers to binding molecules, preferably proteins, antibodies, or DNA. Generally, chromatography uses biologically active surfaces as adsorbents to selectively accumulate certain biomolecules, e.g., biomarkers.

The phrase "mass spectrometry" refers to a method comprising employing an ionization source to generate gas phase ions from a biological entity of a sample presented on a biologically active surface, and detecting the gas phase ions with an ion detector. Comparison of the time gas phase ions take to reach an ion detector from the moment of ionization with a calibration equation derived from at least one molecule of known mass allows the calculation of the estimated mass to charge ratio of the ion being detected.

The phrases "mass to charge ratio", "m/z ratio" or "m/z" can be used interchangeably and refer to the ratio of the molecular weight (grams per mole) of an ion detected by mass spectrometry to the number of charges the ion carries. Thus a single biomolecule can be assigned more than one mass to charge ratio by a mass spectrometer if that biomolecule can be ionized into more than one species each of which carries a different number of charges.

The acronym "TOF" refers to the time-of-flight of a biomolecule or other molecular entity, particularly that of an ion in a time-of-flight type mass spectrometer. TOF values are derived by measuring the duration of flight of an ion, typically between its entry into and exit from a time-of-flight analyzer tube. In an embodiment, the accuracy of TOF values can be improved by methods known to those skilled in the art, for example through the use of reflectrons and/or pulsed-laser ionization. TOF values for a given ion can be applied to previously established calibration equations derived from the TOF values for ions of known mass in order to calculate the mass to charge ratio of these ions.

The phrase "laser desorption mass spectrometry" refers to a method comprising the use of a laser as an ionization source to generate gas phase ions from a biomolecule presented on a biologically active surface, and detecting the gas phase ions with a mass spectrometer.

The term "mass spectrometer" refers to a gas phase ion spectrometer that includes an inlet system, an ionization source, an ion optic assembly, a mass analyzer, and a detector.

Within the context of the invention, the terms "detect", "detection" or "detecting" refer to the identification of the presence, absence, or quantity of a given biomarker.

The phrase "energy absorbing molecule" and its acronym "EAM" refers to a molecule that absorbs energy from an energy source in a mass spectrometer thereby enabling desorption of a biomolecule from a biologically active surface. Cinnamic acid derivatives, sinapinic acid and dihydroxybenzoic acid, ferulic acid and caffeic acid are frequently used as energy-absorbing molecules in laser desorption of biomolecules. See U.S. Pat. No. 5,719,060 for a further description of energy absorbing molecules.

The terms "peak" and "signal" may be used interchangeably, and refer to a defined, non-background value which is generated by a population of a given biomolecule of a certain molecular mass that has been ionized contacting the detector of a mass spectrometer, wherein the size of the population can be roughly related to the degree of the intensity of the signal. Typically, this "signal" can be defined by two values: an apparent mass-over-charge ratio (m/z) and an intensity value generated as described.

The phrases "peak intensity", "intensity of a peak" and "intensity" may be used interchangeably, and refer to the relative amount of a biomolecule contacting the detector of a mass spectrometer in relation to other peaks in the same mass profile. Typically, the intensity of a peak is expressed as the maximum observed signal within a defined mass range that adequately defines the peak.

The phrases "signal to noise ratio", "SN ratio" and "SN" may be used interchangeably, and refer to the ratio of a peak's intensity and a dynamically calculated value representing the average background signal detected in the approximate mass range of the peak. The SN ratio of a peak is typically used as an objective criterion for (a) computer-assisted peak detection and/or (b) manual evaluation of a peak as being an artifact.

The acronym "ROC-AUC" refers to the area under a receiver operator characteristic curve. This is a widely accepted measure of diagnostic utility of some tool, taking into account both the sensitivity and specificity of the tool. Typically, ROC-AUC ranges from 0.5 to 1.0, where a value of 0.5 indicates the tool has no diagnostic value and a value of 1.0 indicates the tool has 100% sensitivity and 100% specificity.

The term "sensitivity" refers to the proportion of patients with the outcome in whom the results of the decision rule are abnormal. Typically, the outcome is disadvantageous to the patient. The term "specificity" refers to the proportion of patients without the outcome in whom the results of the decision rule are normal.

Diagnostic Methods

The present invention relates to methods for differential diagnosis of prostate cancer by detecting one or more differentially expressed biomarkers within a biological sample of a given subject, wherein the presence or absence of the biomarkers allows for the differential diagnosis of a subject as healthy or having prostate cancer. In one embodiment, the methods detect the presence of a biomarker in a sample wherein the marker is not expressed in healthy, disease-free individuals. In related embodiments, the methods of the invention detect elevated levels of biomarkers that are present at higher levels in samples from individuals that have cancer, e.g., prostate cancer, as compared to normal, healthy individuals.

In one embodiment, the diagnostic methods of the invention are particularly useful in subjects that have PSA levels of less than 10. Accordingly, the instant invention provides methods for the early detection of prostate cancer in subjects who, using currently available methods, would not be diagnosed with prostate cancer until the disease progresses, i.e., until the PSA levels in these subjects reached a higher level.

In one aspect of the invention, a method for the differential diagnosis of prostate cancer comprises: obtaining a biological sample from a given subject, contacting said sample with an adsorbent present on a biologically active surface under specific binding conditions, allowing the biomarkers within the biological sample to bind to said adsorbent, detecting one or more bound biomarker using a detection method, wherein the detection method generates a mass profile of said sample, transforming the mass profile generated into a computer-readable form, and comparing the mass profile of said sample with a database containing mass profiles from comparable samples specific for healthy subjects, subjects having prostate cancer, and/or subjects having a non-malignant disease of the large intestine. The outcome of said comparison will allow for the determination of whether the subject from which the biological sample was obtained, is healthy, has a non-malignant disease of the large intestine and/or prostate cancer based on the presence, absence or comparative quantity of specific biomolecules.

In more than one embodiment, a single biomarker or a combination of more than one biomarker selected from the group set forth in Table 1 may be detected within a given biological sample.

In yet another aspect of the invention, a biomarker set forth in Table 1 may be used in combination with another diagnostic tool to diagnose a subject as being healthy or having prostate cancer. For example, biomarker membrane metallo endopeptidase (MME) or gamma-glutamyltranspeptidase 1 (GGT1) may be used in combination with other diagnostic tools specific for prostate cancer detection such as, but not limited to, rectal palpitation, biopsy evaluation using Gleason scoring, radiography and symptomological evaluation by a qualified clinician or determination of PSA levels.

Methods for detecting biomarkers have many applications. For example, a single biomarker or a combination of more than one biomarker comprising a biomarker set forth in Table 1 can be measured to differentiate between healthy subjects or subjects having prostate cancer, and thus are useful as an aid in the diagnosis of a subject. In an embodiment, said biomarkers may be used to diagnose a subject as being healthy.

For example, biomarker gamma-glutamyltranspeptidase 1 (GGT1) may be present only in biological samples from patients having prostate cancer. Mass profiling of two biological samples from different subjects, X and Y, can reveal the presence of biomarker gamma-glutamyltranspeptidase 1 (GGT1) in a sample from test subject X, and the absence of the same biomarker in a test sample from subject Y. The medical practitioner can diagnose subject X as having prostate cancer and subject Y as not having prostate cancer.

In yet another example, one or more biomarkers set forth in Table 1 can be present in varying quantities in samples specific for benign prostatic hyperplasia (BPH) and prostate cancer.

In another aspect of the invention, an in vitro binding assay can be used to detect a biomarker set forth in Table 1 in a biological sample of a given subject. A given biomarker of the invention can be detected within a biological sample by contacting the biological sample from a given subject with specific binding molecule(s) under conditions conducive for an interaction between the given binding molecule(s) and a biomarker set forth in Table 1. If a given biomarker is present in the biological sample, it will form a complex with its binding molecule. To determine if the quantity of the detected biomarker in a biological sample is comparable to a given quantity for healthy subjects, the amount of the complex formed between the binding molecule and a biomarker can be determined by comparing to a standard. For example, if the amount of the complex falls within a quantitative value for healthy subjects, then the sample can be considered to be obtained from a healthy subject. If the amount of the complex falls within a quantitative value for subjects known to have a non-malignant disease of the large intestine, then the sample can be considered to be obtained from a subject having a non-malignant disease of the large intestine. If the amount of the complex falls within a quantitative range for subjects known to have prostate cancer, then the sample can be considered to have been obtained from a subject having prostate cancer. In vitro binding assays that are included within the scope of the invention are well known (e.g., ELISA, western blotting).

Thus, an embodiment of the invention provides a method for the differential diagnosis of prostate cancer: detecting of one or more differentially expressed biomarkers comprising a biomarker set forth in Table 1 within a given biological sample. This method comprises obtaining a biological sample from a subject, contacting said sample with a binding molecule specific for a differentially expressed biomarker, detecting an interaction between the binding molecule and its specific biomarker, wherein the detection of an interaction indicates the presence or absence of said biomarker, thereby allowing for a differential diagnosis of a subject as healthy, or having a prostate cancer.

Binding molecules include, but are not limited to, nucleic acids, nucleotides, oligonucleotides, polynucleotides, amino acids, peptides, polypeptides, proteins, monoclonal and/or polyclonal antibodies, antigens, sugars, carbohydrates, fatty acids, lipids, steroids, compounds, synthetic molecules or combinations thereof. (e.g. glycoproteins, ribonucleoproteins, lipoproteins). Preferably, binding molecules can be antibodies specific for at least one of the biomarkers set forth in Table 1. Biomarkers detected using the above-mentioned binding molecules include, but are not limited to, molecules comprising nucleic acids, nucleotides, oligonucleotides, polynucleotides, amino acids, peptides, polypeptides, proteins, monoclonal and/or polyclonal antibodies, antigens, sugars, carbohydrates, fatty acids, lipids, steroids, and combinations thereof (e.g., glycoproteins, ribonucleoproteins, lipoproteins). Preferably, biomarkers that are detected using the above-mentioned binding molecules include, nucleic acids, nucleotides, oligonucleotides, polynucleotides, amino acids, peptides, polypeptides, proteins, monoclonal and/or polyclonal antibodies. Even more preferred are binding molecules that are amino acids, peptides, polypeptides, proteins, monoclonal and/or polyclonal antibodies.

For example, in vivo antibodies or fragments thereof may be utilized for detecting a biomarker in a biological sample comprising: applying a labeled antibody specific for a biomarker to a biological sample under conditions that favor an interaction between the labeled antibody and its corresponding biomarker. For example, in a blood serum sample, only the serum levels of a given biomolecule can be detected, whereas its level of expression and cellular localization can be detected in histological samples. A wide variety of methods can be modified in order to achieve such detection.

Furthermore, in vivo techniques for detecting a biomolecule comprising a biomarker set forth in Table 1 include introducing into a subject a labeled antibody specific for a biomarker set forth in Table 1.

In addition, methods of the invention for the differential diagnosis of healthy subjects or subjects having a prostate cancer may be combined with other diagnostic methods to improve the outcome of the differential diagnosis. Other diagnostic methods such as PSA screening are well known.

Molecules of the Invention

Differential expression of biomarkers in samples from healthy subjects and subjects having prostate cancer allows for a differential diagnosis of prostate cancer within a given subject. Accordingly, biomarkers characterized herein can be isolated and further characterized using standard laboratory techniques, and used to determine novel treatments for prostate cancer. Knowledge of the association of these biomarkers with prostate cancer can be used, for example, to treat patients with the biomarker, an antibody specific to the biomarker, or an antagonist of the biomarker.

Biomarkers are said to be specific for a particular clinical state (e.g., healthy or prostate cancer, when the biomarkers are present at different levels within samples taken from subjects in one clinical state compared to samples taken from subjects from other clinical states (e.g., in subjects with cancer vs. healthy subjects. Biomarkers may be present at elevated levels, at decreased levels, or altogether absent within a sample taken from a subject in a particular clinical state (e.g., healthy or having prostate cancer).

Accordingly, differential presence of one or more biomarkers found in a given biological sample provides useful information regarding a probability of whether a subject being tested has prostate cancer or is healthy. A probability that a subject being tested has prostate cancer or is healthy depends on whether the quantity of one or more biomarkers in a test sample taken from said subject is statistically significant from a quantity of one or more biomarkers in a biological sample taken from healthy subjects or a control level known to exist in health subjects.

A differential presence of one or more biomarkers found in a given biological sample may also be used to determine whether a subject known to have a prostate cancer is responding to a therapeutic treatment being administered. A quantity of one of more said biomarkers detected in a sample taken at time of therapy is compared to a quantity of one of more said biomarkers detected in a sample taken prior to an administration of treatment. In addition, a quantity of one or more said biomarkers detected in a sample taken at time of therapy is compared to a reference biomarker panel indicative of a healthy subject. Based on a comparison, one can determine whether said subject is responding to a therapeutic treatment, and to what degree the response is.

Furthermore, a differential presence of one or more biomarkers found in a given biological sample may also be used to determine whether a subject known to have a prostate cancer will respond to a given therapeutic treatment. A quantity of one or more said biomarkers detected in a sample taken from a subject diagnosed as having a prostate cancer is compared to reference biomarker panels taken from subjects with similar diagnoses that have undergone different forms of treatment. Reference biomarker panels generated from samples taken from subjects exposed to a given treatment, wherein the treatment resulted in a positive outcome are considered to indicate that the given treatment had a positive effect on the subject and therefore would be deemed successful. Reference biomarker panels generated from samples taken from subjects exposed to a given treatment, wherein the treatment resulted in a neutral outcome are considered to indicate that the given treatment had no therapeutic effect on the subject and would therefore be deemed unsuccessful. Reference biomarker panels generated from samples taken from subjects exposed to a given treatment, wherein the treatment resulted in a negative outcome are considered to indicate that the given treatment had no therapeutic effect on the subject and would be deemed unsuccessful. Based on the comparison, one skilled in the art would be able to administer the best mode of treatment for said subject.

Additionally, differential presence of one or more biomolecules found in a given biological sample may also be used to determine the stage of prostate cancer in a subject. A quantity of one or more said biomarkers detected in a sample taken from a subject diagnosed as having a prostate cancer is compared to reference biomarker panel taken from subjects known to have a specific stage or grade of prostate cancer. Based on the comparison, one would be able to determine the stage or grade at which the prostate cancer within said subject.

Screening for Therapeutics

Differential expression of biomarkers may be the result of an aberrant expression of said biomarkers at either the genomic (e.g., gene amplification), transcriptomic (e.g., increased mRNA), or proteomic levels (i.e. translation, post-translational modifications etc.) within a given subject. Whereas aberrant over-expression of biomarkers may be regulated using agents that inhibit its biological activity and/or biological expression, aberrant under-expression of a given biomolecule may be regulated using agents that can promote its biological activity or biological expression. Such agents can be used to treat a subject known to have prostate cancer and are, therefore, referred to as therapeutic agents.

Embodiments of the invention provide methods for screening therapeutic agents for treating prostate cancer resulting from aberrant expression of a biomarker set forth in Table 1. Methods identify agents (e.g. peptides, peptidomimetics, nucleic acid molecules, small molecules or other drugs), or candidate test molecules or compounds, which may decrease the expression of a biomarker are provided by the instant invention.

Furthermore, embodiments of the invention provide methods for screening therapeutic agents for treating prostate cancer resulting from aberrant expression of a biomarker. The methods identify candidates, test molecules or compounds, or agents (e.g. peptides, peptidomimetics, nucleic acid molecules, small molecules or other drugs), which may decrease or increase the biological activity of a biomarker set forth in Table 1.

Agents capable of interacting directly or indirectly with a biomarker selected from the group of set forth in Table 1, can be identified by various methods. For example, such agents can be identified using methods based on various binding assays (see references on: yeast-2-hybrid (Bemis et al., 1995; Fields & Sternglanz, 1994; Topcu & Borden, 2000); yeast 3 hybrid: (Zhang et al., 1999); GST pull-downs (Palmer et al., 1998); and phage display (Scott & Smith, 1990)).

One embodiment provides assays for screening agents that bind to, interact with, or modulate a biologically active form of a biomolecule comprising a biomarker M1, M2, M3, M4, M5, or M6. Agents can be obtained using any of the numerous known approaches in combinatorial library methods, including: biological libraries, spatially addressable parallel solid phase or solution phase libraries, synthetic library methods requiring deconvolution, the 'one-bead-one-compound' library method, and synthetic library methods using affinity chromatography selection. The biological library approach is limited to peptide libraries, while the other four approaches are applicable to peptide, non-peptide oligomer or small molecule libraries of compounds (Bindseil et al., 2001; Grabley et al., 2000; Houghten et al., 2000; Rader, 2001).

Examples of methods for the synthesis of molecular libraries are well known, for example, (DeWitt, Erb, Gallop and Gordon).

Libraries of agents may be presented in solution (Houghten, 1992), or on beads (Lam et al., 1991), chips (Fodor et al., 1993), bacteria (U.S. Pat. No. 5,223,409), spores (U.S. Pat. Nos. 5,571,698; 5,403,484; and 5,223,409), plasmids (Cull et al., 1992) or phages (Scott and Smith, 1990; Devlin et al., 1990; Cwirla et al., 1990; Felici et al., 1991).

In one embodiment, an assay is a cell-based assay in which a cell expresses a biomarker. The expressed biomarker is contacted with an agent or a library of agents and the ability of the agent to bind to, or interact with, a polypeptide is determined. The cell can, for example, be a eukaryotic cell such as, but not limited to a yeast cell, an invertebrate cell (e.g. *C. elegans*), an insect cell, a teleost cell, an amphibian cell, or a cell of mammalian origin. Determining an ability of an agent to bind to, or interact with a biomarker of the invention can be accomplished, for example, by coupling an agent with a radioisotope or enzymatic label (e.g., horseradish peroxidase, alkaline phosphatase, or luciferase) such that binding or interaction of the agent to a biomolecule can be determined by detecting the labelled agent in the complex. Methods of labelling and detecting interactions of agents with a biomolecule are well known.

In a preferred embodiment, an assay comprises contacting a cell, that expresses a biomarker set forth in Table 1, with a known agent which binds or interacts with a biomarker of Table 1 to form an assay mixture, contacting the assay mixture with a test agent, and determining the ability of the test agent to bind to or interact with a biomarker of the invention, wherein determining the ability of the test agent to bind or interact with a biomarker is compared to a control biomolecule. Determination of the ability of a test agent to bind to or interact with a biomarker is based on competitive binding/inhibition kinetics of the test agent and known target agent for a given biomarker. Methods of detecting competitive binding or the interaction of two molecules for the same target, wherein the target is a biomarker, are well known.

In another embodiment, an assay is a cell-based assay comprising contacting a cell expressing a biologically active biomarker, with a test agent and determining the ability of the test agent to inhibit a biological activity of a biomarker. This can be accomplished, for example, by determining whether a biomarker continues to bind to or interact with a known target molecule, or whether a specific cellular function has been abrogated. For example, a target molecule can be a component of a signal transduction pathway that facilitates transduction of an extracellular signal, a second intercellular protein that has a catalytic activity, a protein that regulates transcription of specific genes, or a protein that initiates protein translation. Determining the ability of a biologically active biomarker to bind to or interact with a target molecule can be accomplished by determining the activity of the target molecule. For example, an activity of a target molecule can be determined by detecting induction of a cellular second messenger of the target, detecting catalytic/enzymatic activity of the target on an appropriate substrate, detecting the induction (via a regulatory element that may be responsive to a given polypeptide) of a reporter gene operably linked to a polynucleotide encoding a detectable marker (e.g., (3-galactosidase, luciferase, green fluorescent protein (GFP), enhanced green fluorescent protein (EGFP), Ds-Red fluorescent protein, far-red fluorescent protein (Hc-red), secreted alkaline phosphatase (SEAP), chloramphenicol acetyltransferase (CAT), neomycin, etc.), or detecting a cellular response, for example, cellular differentiation, proliferation or migration.

In yet another embodiment, an assay can be a cell-free assay comprising contacting a biologically active biomarker with a test agent, and determining the ability of the test agent to bind to or interact with any one of the biomarkers. Binding or interaction of a test agent to a biomarker can be determined either directly or indirectly as described above. In a preferred embodiment, an assay includes contacting any one of the biomarkers with a known agent, that binds or interacts with said biomarker to form an assay mixture. An assay mixture is contacted with a test agent, and a determination of the ability of the test agent to interact with the polypeptide is based on competitive binding/inhibition kinetics of the test agent and known agents for a given biomarker. Methods of detecting competitive binding, or interaction, of two agents for the same biomolecule are well known.

In another embodiment, an assay is a cell-free assay comprising contacting a biologically active biomarker comprising a biomarker M1, M2, M3, M4, M5, or M6, with a test agent, and determining the ability of the test agent to inhibit an activity of a given biomarker. Determining the ability of the test agent to inhibit an activity of a biomarker can be accomplished, for example, by determining the ability of a biomarker to bind to a target molecule by one of the methods described herein for determining direct binding. In an alternative embodiment, determining the ability of the test agent to modulate an activity of a given biomarker can be accomplished by determining the ability of a given biomarker to further modulate a target molecule.

In another embodiment, inhibitors of expression of a biomarker are identified in a method in which cells are contacted with a candidate agent and/or library of candidate agents, and the expression of a selected mRNA or protein (i.e., the mRNA or protein corresponding to at least one of biomarkers set forth in Table 1 or a biologically active biomarker of the invention) in a cell is determined. In a preferred embodiment, the cell is an animal cell. Even more preferred, the cell can be derived from an insect, fish, amphibian, mouse, rat, or human. The level of expression of a selected mRNA or protein in the presence of a candidate agent is compared to the level of expression of the selected mRNA or protein in the absence of a candidate agent. A candidate agent can be identified as a inhibitor of expression of a given biomarker based on this comparison. For example, when expression of a selected mRNA or protein is less (statistically significant) in the presence of a candidate agent than in its absence, the candidate agent is identified as an inhibitor of the selected mRNA or protein expression. The level of the selected mRNA or protein expression in the cells can be determined by methods described herein.

Those test agents identified in the above-described assays are considered within the context of the invention as specific therapeutic agents.

In another embodiment, a therapeutic agent can also be identified by using a reporter assay, in which the level of expression of a reporter construct, under the control of a biomarker gene promoter, is measured in the presence or absence of a test agent. A biomarker promoter can be isolated by screening a genomic library with a cDNA encoding the complete coding sequence for a biomarker; preferably containing the 5' end of the cDNA. A portion of said promoter, typically from 20 to about 500 base pairs long is then cloned upstream of a reporter gene, e.g., a β-galactosidase, luciferase, green fluorescent protein (GFP), enhanced green fluorescent protein (EGFP), Ds-Red fluorescent protein, far-red fluorescent protein (Hc-red), secreted alkaline phosphatase (SEAP), chloramphenicol acetyltransferase (CAT), neomycin gene, in a plasmid. This reporter construct is then transfected into cells, e.g., mammalian cells. The transfected cells are distributed into wells of a multi-well plate and various concentrations of test molecules or compounds are added to the wells. After several hours of incubation, the level of expression of the reporter construct is determined according to known methods. A difference in the level of expression of the reporter construct in transfected cells incubated with the test molecule or compound relative to transfected cells incubated without the test molecule or compound will indicate that the test molecule or compound is capable of modulating the expression of a gene encoding a biomarker and is thus a therapeutic agent for the biomarker.

In one embodiment of the invention, therapeutic agents for a biomarker can be used for treating prostate cancer, and may be administered to any patient in need of such therapy. Preferably, the patient in need of such therapy is of human origin.

Biological Samples of the Invention

Although said biomarker were first identified in serum samples, their detection is not limited to said sample type. In more than one embodiment of the invention, biomolecules can be detected in blood, plasma, urine, semen, seminal fluid, seminal plasma, pre-ejaculatory fluid (Cowper's fluid), excreta, tears, saliva, sweat, biopsy, ascites, cerebrospinal fluid, lymph, or tissue extract (biopsy) samples. Preferably, biological samples used to detect biomolecules are of urine, blood, serum, plasma and excreta.

Furthermore, biological samples used for methods of the invention are isolated from subjects of mammalian origin, preferably of primate origin. Even more preferred are male subjects of human origin.

A subject that is said to have prostate cancer possesses morphological, biochemical, and functional alterations of their prostate tissue such that the tissue can be characterized as a malignant neoplasm. The stage to which a prostate cancer has progressed can be determined using known methods currently available and presented herein. Currently, the most widely used method for determining the extent of malignancy of a prostate neoplasm is the Gleason Grading system. Gleason grading is based exclusively on the architectural pattern of the glands of a prostate neoplasm, wherein the ability of neoplastic cells to structure themselves into glands resembling those of the normal large intestine is evaluated using a scale of 1 to 5. For example, neoplastic cells that are able to architecturally structure themselves such that they resemble normal gland structure are graded 1-2, whereas neoplastic cells that are unable to do so are graded 4-5. A prostate neoplasm has tumor structure that is nearly normal will tend to behave, biologically, as normal tissue and therefore it is unlikely that it will be aggressively malignant.

A subject that is said to have non-malignant disease of the large intestine possesses morphological and/or biochemical alterations of their prostate tissue but does not exhibit malignant neoplastic properties. Such diseases include, but are not limited to, inflammatory and proliferative lesions, as well as benign disorders of the large intestine. Within the context of the invention, inflammatory diseases encompass inflammatory bowel diseases including but not limited to Crohn's disease, ulcerative colitis, and proliferative lesions include benign large intestine hyperplasia.

Detection of Biomarker of the Invention

In one embodiment, mass spectrometry can be used to detect biomarkers in a given sample. Such methods include, but are not limited to, matrix-assisted laser desorption ionization/time-of-flight (MALDI-TOF), surface-enhanced laser desorption ionization/time-of-flight (SELDI-TOF), liquid chromatography coupled with MS, MS-MS, ESI-MS, immunohistochemistry, or gel electrophoresis.

In preferred embodiments, the biomarkers of the invention are detected using mass spectrometry or immunohistochemistry. In one embodiment, matrix-assisted laser desorption/ionization ("MALDI") mass spectrometry can be used. In MALDI, the sample is partially purified to obtain a fraction that essentially consists of a biomolecule by employing such separation methods as: two-dimensional gel electrophoresis (2D-gel) or high performance liquid chromatography (HPLC).

In another embodiment, surface-enhanced laser desorption/ionization mass spectrometry (SELDI) can be used to detect a biomarker uses a substrate comprising adsorbents to capture biomarkers, which can then be directly desorbed and ionized from the substrate surface during mass spectrometry. Since the substrate surface in SELDI captures biomarkers, a sample need not be partially purified as in MALDI. However, depending on the complexity of a sample and the type of adsorbents used, it may be desirable to prepare a sample to reduce its complexity prior to SELDI analysis.

In another embodiment, the inventors have developed a novel method for isolating, identifying and detecting biomarkers for prostate cancer. Specifically, the inventors have developed a method for identifying biomarkers of prostate cancer using a system of solid phase extraction of N-linked glycopeptides (SPEG) and then analyzing these peptides by mass spectrometry. For a review of SPEG see, Zhang et al. (2005) Mol. Cell Proteomics 4:144-55. This novel method is presented in detail in the Examples. Accordingly, in one embodiment, the biomarkers of the invention are detected using mass spectrometry wherein a known amount of a heavy-isotope labeled peptide is added to the sample to enable accurate detection of the biomarker. Exemplary heavy isotope labeled peptides are set forth in Table 1.

In one embodiment, a laser desorption time-of-flight mass spectrometer is used with the probe of the present invention. In laser desorption mass spectrometry, biomarkers bound to a biologically active surface are introduced into an inlet system. Biomarkers are desorbed and ionized into the gas phase by a laser. The ions generated are then collected by an ion optic assembly. These ions are accelerated through a short high-voltage field and allowed to drift into a high vacuum chamber of a time-of-flight mass analyzer. At the far end of the high vacuum chamber, the accelerated ions collide with a detector surface at varying times. Since the time-of-flight is a function of the mass of the ions, the elapsed time between ionization and impact can be used to identify the presence or absence of molecules of a specific mass.

Data analysis can include the steps of determining signal strength (e.g., intensity of peaks) of a biomarker(s) detected and removing "outliers" (data deviating from a predetermined statistical distribution). An example is the normalization of peaks, a process whereby the intensity of each peak relative to some reference is calculated. For example, a reference can be background noise generated by an instrument and/or a chemical (e.g., energy absorbing molecule), which is set as zero in the scale. Then the signal strength detected for each biomarkers can be displayed in the form of relative intensities in the scale desired (e.g., 100). In an embodiment, an observed signal for a given peak can be expressed as a ratio of the intensity of that peak over the sum of the entire observed signal for both peaks and background noise in a specified mass to charge ratio range. In an embodiment, a standard may be admitted with a sample so that a peak from the standard can be used as a reference to calculate relative intensities of the signals observed for each biomarker(s) detected.

The resulting data can be transformed into various formats for displaying, typically through the use of computer algorithms. In one format, referred to as a "spectrum view", a standard spectral view can be displayed, wherein the view depicts the quantity of a biomarker reaching the detector at each possible mass to charge ratio. In another format, referred to as "scatter plot", only the intensity and mass to charge information for defined peaks are retained from the spectrum view, yielding a cleaner image and enabling biomarkers with nearly identical molecular mass to be more easily distinguished from one another.

Using any of the above display formats, it can be readily determined from a signal display whether a biomarker having a particular TOF is detected from a sample. Preferred biomarkers of the invention are biomarkers set forth in Table 1.

In another aspect of the invention, biomarkers can be detected using other methods known to those skilled in the art. For example an in vitro binding assay can be used to detect a biomarker of the invention within a biological sample of a given subject. A given biomarker of the invention can be detected within a biological sample by contacting the biological sample from a given subject with specific binding molecule(s) under conditions conducive for an interaction between the given binding molecule(s) and a biomarker. Binding molecules include, but are not limited to, nucleic acids, nucleotides, oligonucleotides, polynucleotides, amino acids, peptides, polypeptides, proteins, monoclonal and/or polyclonal antibodies, antigens, sugars, carbohydrates, fatty acids, lipids, steroids, or combinations thereof. (e.g. glycoproteins, ribonucleoproteins, lipoproteins), compounds or synthetic molecules. Preferably, binding molecules are antibodies specific for any one of the biomarkers set forth in Table 1. The biomarkers detected using the above-mentioned binding molecules include, but are not limited to, molecules comprising nucleic acids, nucleotides, oligonucleotides, polynucleotides, amino acids, peptides, polypeptides, proteins, monoclonal and/or polyclonal antibodies, antigens, sugars, carbohydrates, fatty acids, lipids, steroids, and combinations thereof (e.g., glycoproteins, ribonucleoproteins, lipoproteins). Preferably, biomarkers that are detected using the above-mentioned binding molecules include peptides and polypeptides.

Antibodies of the Invention

With respect to protein-based testing, antibodies can be generated to the biomarkers using standard immunological techniques, fusion proteins or synthetic peptides as described herein. Monoclonal antibodies can also be produced using now conventional techniques such as those described in Waldmann (1991) and Harlow and Lane (1988). It will also be appreciated that antibody fragments, i.e. Fab' fragments, can be similarly employed. Immunoassays, for example ELISAs, in which the test sample is contacted with antibody and binding to the biomarker detected, can provide a quick and efficient method of determining the presence and quantity of the biomarker. For example, the antibodies can be used to test the effect of pharmaceuticals in subjects enrolled in clinical trials. Moreover, antibodies that specifically recognize a number of biomarkers of the invention are commercially available.

Thus, embodiments of the invention also provide polyclonal and/or monoclonal antibodies and fragments thereof, and immunologic binding equivalents thereof, which are capable of specifically binding to the biomarkers and fragments thereof. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into a host mammal. The host's sera can be tested for immunoreactivity to the subject polypeptide or fragment. Monoclonal antibodies may be made by injecting mice with the protein polypeptides, fusion proteins or fragments thereof. Monoclonal antibodies are screened by ELISA and tested for specific immunoreactivity with subject biomarkers or fragments thereof (Harlow & Lane, 1988). These antibodies are useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical routes for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art, such as in Harlow and Lane (1988) or Goding (1996).

Monoclonal antibodies with affinities of $10^8$ $M^{-1}$ or preferably $10^9$ to $10^{10}$ $M^{-1}$ or stronger will typically be made by standard procedures as described in Harlow and Lane (1988) or Goding (1996). Briefly, appropriate animals will be selected and the desired immunization protocol followed. After an appropriate period of time, spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

The polypeptides and antibodies of the present invention may be used with or without modification. Frequently, polypeptides and antibodies will be labeled by joining, either covalently or non-covalently, a substance, which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

Generation of Monoclonal Antibodies Specific for the Biomarker

Monoclonal antibodies can be generated according to various known methods. For example any technique that provides for production of antibody molecules by continuous cell lines in culture may be used. These include but are not limited to the hybridoma technique originally developed by Kohler and Milstein (1975), as well as the trioma technique, the human B-cell hybridoma technique (Kozbor et al., 1983); (Cote et al., 1983), and the EBV-hybridoma technique to produce human monoclonal antibodies (Cole et al., 1985). In fact, according to the invention, techniques developed for production of "chimeric antibodies" (Morrison et al., 1984; Neuberger et al., 1984; Takeda et al., 1985) by splicing the genes from a mouse antibody molecule specific for a given biomarker of the invention together with genes from a human antibody molecule of appropriate biological activity can be used. Such human or humanized chimeric antibodies are preferred for use in therapy of human diseases or disorders (described infra), since human or humanized antibodies are much less likely than xenogeneic antibodies to induce an immune response, in particular an allergic response, themselves.

The following example of monoclonal antibody production is meant for clarity and is not intended to limit the scope of the invention. One method of producing antibodies of the invention is by inoculating a host mammal with an immunogen comprising an intact subject biomarker or its peptide (wild or mutant). A host mammal may be any mammal and is preferably a host mammal such as a mouse, rat, rabbit, guinea pig or hamster and is most preferably a mouse. By inoculating a host mammal, it is possible to elicit the generation of antibodies directed towards the immunogen introduced into the host mammal. Several inoculations may be required to elicit an immune response.

To determine if the host mammal has developed antibodies directed towards the immunogen, serum samples are taken from the host mammal and screened for the desired antibodies. This can be accomplished by known techniques such as radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on a primary antibody. In another embodiment, a primary antibody is detected by detecting binding of a secondary antibody or reagent to the primary antibody. In a further embodiment, a secondary antibody is labeled.

Once antibody generation is established in a host mammal, it is selected for hybridoma production. The spleen is removed and a single cell suspension is prepared as described by Harlow and Lane (1988). Cell fusions are performed essentially as described by Kohler and Milstein (1975). Briefly, P3.65.3 myeloma cells (American Type Culture Collection, Manassas, Va.) are fused with immune spleen cells using polyethylene glycol as described by Harlow and Lane (1988). Cells are plated at a density of 2.times.10.sup.5 cells/well in 96 well tissue culture plates. Individual wells are examined for growth and the supernatants of wells with growth are tested for the presence of subject biomarker specific antibodies by ELISA or RIA using wild type or mutant target protein. Cells in positive wells are expanded and subcloned to establish and confirm monoclonality. Clones with the desired specificities are expanded and grown as ascites in mice or in a hollow fiber system to produce sufficient quantities of antibody for characterization and assay development.
Antibody based Assay for the Biomarker Sandwich assays for the detection of a biomarker can be used as a diagnostic tool for the diagnosis of a subject as being healthy or having prostate cancer. Sandwich assays consist of attaching a monoclonal antibody to a solid surface such as a plate, tube, bead, or particle, wherein an antibody is preferably attached to the well surface of a 96-well microtitre plate. A pre-determined volume of sample (e.g., serum) potentially containing the subject biomarker can be added to the solid phase antibody, and the sample can be incubated for a period of time at a pre-determined temperature conducive for the specific binding of the subject markers within the given sample to the solid phase antibody. Following, a sample fluid can be discarded, and the solid phase can be washed with buffer to remove any unbound material. A volume of a second monoclonal antibody (to a different determinant on the subject biomarker) can be added to the solid phase. This antibody can be labeled with a detector molecule or atom (e.g., enzyme, fluorophore, chromophore, or $^{125}$I) and the solid phase with the second antibody can be incubated for two hrs at room temperature. The second antibody can be decanted, and the solid phase can be washed with buffer to remove unbound material.

The amount of bound label, which is proportional to the amount of subject biomarker present in the sample, can be quantitated.

In alternative embodiments, the assay can be an ELISA to determine the presence and/or amount of one or more biomarkers in a sample.

Kits of the Invention

Yet another aspect of the invention provides kits using the methods of the invention for differential diagnosis of prostate cancer, wherein the kits are used to detect one or more biomarkers set forth in Table 1.

Methods used to detect biomarkers can also be used to determine whether a subject is at risk of developing prostate cancer or has developed prostate cancer. Such methods may also be employed in the form of a diagnostic kit comprising a binding molecule specific to a biomarker solutions, and materials necessary for the detection of a biomarkers of the invention, and instructions to use the kit based on the above-mentioned methods. In one exemplary embodiments, the kits of the invention may contain one or more antibodies or one or more labeled peptides and instructions for use.

For example, kits can be used to detect one or more biomarkers. Kits of the invention have many applications. For example, the kits can be used to differentiate if a subject is healthy, or has prostate cancer, thus aiding the diagnosis of prostate cancer. Moreover, the kits can be used to differentiate if a subject is healthy.

In some embodiments, a kit may comprise a first substrate comprising an adsorbent thereon (e.g., a particle functionalized with an adsorbent) and a second substrate onto which the first substrate can be positioned to form a probe, which is removably insertable into a gas phase ion spectrometer. In other embodiments, a kit may comprise a single substrate, which is in the form of a removably insertable probe with adsorbents on the substrate.

In another embodiment, a kit comprises a binding molecule or panel of binding molecules that specifically binds to a biomarker or biomarkers, a detection reagent, appropriate solutions and instructions on how to use the kit. Such kits can be prepared from the materials described above, and other materials known to those skilled in the art. A binding molecule used within such a kit may include, but is not limited to, nucleic acids, nucleotides, oligonucleotides, polynucleotides, amino acids, peptides, polypeptides, proteins, monoclonal and/or polyclonal antibodies, sugars, carbohydrates, fatty acids, lipids, steroids, hormones, or a combination thereof (e.g. glycoproteins, ribonucleoproteins, lipoproteins), compounds or synthetic molecules).

In an embodiment, a kit may optionally further comprise a standard or control biomolecule so that the biomarkers detected within a biological sample can be compared with said standard to determine if the test amount of a marker detected in a sample is a diagnostic amount consistent with a diagnosis prostate cancer. Likewise a biological sample can be compared with said standard to determine if the test amount of a marker detected is said sample is a diagnostic amount consistent with a diagnosis as healthy.

Composition, Formulation, and Administration of Pharmaceutical Compositions.

Differential expression of biomarkers in samples from healthy subjects and subjects having prostate cancer allows for a differential diagnosis of prostate cancer in a given subject. Accordingly, biomarkers discovered and characterized herein can be isolated and further characterized using standard laboratory techniques, and used to determine novel treatments for prostate cancer. Knowledge of the association of these biomolecules with prostate cancer can be used, for example, to treat patients with the biomolecule, an antibody specific to the biomolecule, or an antagonist of the biomolecule.

In order to treat prostate cancer, the biomolecules can be prepared in specific pharmaceutical compositions and or formulations that allow for the most efficient and effective delivery of the therapy.

Pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations, which can be used pharmaceutically. Proper formulation is dependent upon the route of administration chosen.

For injection, agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

]For oral administration, compounds can be formulated readily by combining active compounds with pharmaceutically acceptable carriers known in the art. Such carriers enable compounds of the invention to be formulated as tablets, pills, dragees, capsules, liquids, gels, syrups, slurries, suspensions and the like, for oral ingestion by a patient to be treated. Pharmaceutical preparations for oral use can be obtained by solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol, or cellulose preparations such as, maize starch, wheat starch, rice starch, potato starch, gelatin, gum tragacanth, methyl cellulose, hydroxypropylmethyl-cellulose, sodium carboxymethylcellulose, and/or polyvinylpyrrolidone. If desired, disintegrating agents may be added, such as the cross-linked polyvinylpyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. Push-fit capsules can contain active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

Compounds may be formulated for parenteral administration by injection, e.g., by bolus injection or continuous infusion. Formulations for injection may be presented in unit dosage form, e.g., in ampoules or in multidose containers, with an added preservative. Compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, a suspension may also contain suitable stabilizers or agents which increase the solubility of the compounds to allow for the preparation of highly concentrated solutions.

In an embodiment, an active ingredient may be in powder form for constitution with a suitable vehicle, e.g., sterile pyrogen-free water, before use.

Compounds may also be formulated in rectal compositions such as suppositories or retention enemas, e.g., containing conventional suppository bases such as cocoa butter or other glycerides.

In addition to the formulations described previously, compounds may also be formulated as a depot preparation. Such long acting formulations may be administered by implantation (for example subcutaneously or intramuscularly) or by intramuscular injection. Thus, for example, compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a co-solvent system comprising benzyl alcohol, a nonpolar surfactant, a water-miscible organic polymer, and an aqueous phase. Naturally, the proportions of a co-solvent system may be varied considerably without destroying its solubility and toxicity characteristics. Furthermore, the identity of the co-solvent components may be varied.

In an embodiment, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, compounds may be delivered using a sustained-release system, such as semipermeable matrices of solid hydrophobic polymers containing therapeutic agent. Various sustained-release materials have been established and are well known. Sustained-release capsules may, depending on their chemical nature, release compounds for a few weeks up to over 100 days. Depending on the chemical nature and the biological stability of therapeutic reagent, additional strategies for protein stabilization may be employed.

Pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Compounds may be provided as salts with pharmaceutically compatible counter ions. Pharmaceutically compatible salts may be formed with many acids, including but, not limited to, hydrochloric, sulfuric, acetic, lactic, tartaric, malic, succinic, etc. Salts tend to be more soluble in aqueous or other protonic solvents than are the corresponding free base forms.

Suitable routes of administration may, for example, include oral, rectal, transmucosal, transdermal, or intestinal administration; or parenteral delivery, including intramuscular, subcutaneous, intramedullary injections, as well as intrathecal, direct intraventricular, intravenous, intraperitoneal, intranasal, or intraocular injections.

Alternately, one may administer a compound in a local rather than systemic manner, for example, via injection of a compound directly into an affected area, often in a depot or sustained release formulation.

Furthermore, one may administer a drug in a targeted drug delivery system, for example, in a liposome coated with an antibody specific for affected cells. Liposomes can be targeted to and taken up selectively by the cells.

Pharmaceutical compositions generally are administered in an amount effective for treatment or prophylaxis of a specific indication or indications. It is appreciated that optimum dosage will be determined by standard methods for each treatment modality and indication, taking into account the indication, its severity, route of administration, complicating conditions and the like. In therapy or as a prophylactic, the active agent may be administered to an individual as an injectable composition, for example, as a sterile aqueous dispersion, preferably isotonic. A "therapeutically effective" dose further refers to that amount of the compound sufficient to result in amelioration of symptoms associated with such disorders. Techniques for formulation and administration of the compounds of the instant application may be found in 'Remington's Pharmaceutical Sciences,' Mack Publishing Co., Easton, Pa., latest edition. For administration to mammals, and particularly humans, it is expected that a daily dosage level of an active agent will be from 0.001 mg/kg to 10 mg/kg, typically around 0.01 mg/kg. A physician in any event will determine the actual dosage, which will be most suitable for an individual and will vary with the age, weight and response of the particular individual. The above dosages are exemplary of the average case. There can, of course, be individual instances where higher or lower dosage ranges are merited, and such are within the scope of this invention.

Compounds may be particularly useful in animal disorders (veterinarian indications), and particularly mammals.

Embodiments of the invention further provide diagnostic and pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

EXAMPLES

It should be appreciated that the invention should not be construed to be limited to the examples that are now described; rather, the invention should be construed to include any and all applications provided herein and all equivalent variations within the skill of the ordinary artisan.

Example 1

Identification of Biomarkers for Prostate Cancer

Materials and Reagents

For glycopeptide capture procedures, Tris (2-carboxythyl) phosphine (TCEP) was purchased from Pierce (Rockford, Ill.); sequencing grade Trypsin was from Promega (Madison, Wis.); peptide-N-glycosidase F (PNGase) was from ProZyme (San Leandro, Calif.); Sequencing grade endoproteinase Arg-C was from Roche (Penzberg, Germany); PSA was from Calbiochem (San Diego, Calif.); Sodium Periodate and Hydrazide resin were from Bio-Rad (Hercules, Calif.); C18 and MCX columns were from Waters (Milford, Miss.); α-cyano-4-cinnamic acid (CHCA) prepared solution was from Aligent (Santa Clara, Calif.). All other chemicals were purchased from Sigma (St. Louis, Mo.). For HPLC chromatography platform, the NanoLC-2D pump was from Eksigent (Dublin, Calif.), the nano-scale MALDI spotter was from Leap technologies (Carrboro, N.C.), and ABI 4800 MALDI TOF/TOF analyzer was from Applied Biosystems (Foster City, Calif.). All trap columns and separation columns were purchased from Dionex (Sunnyvale, Calif.). All HPLC grade reagents used for HPLC-MS analysis were purchased from Fisher Science (Waltham, Mass.). Individual biopsy-positive and biopsy-negative sera, and pooled sera from healthy women_were obtained from the Clinical Chemistry Laboratory at Johns Hopkins University.

The Clinical Samples

Serum specimens for this study were from men aged 52-78 with biopsy-positive (n=9) or biopsy-negative (n=10) groups with PSA concentrations less than 10 ng/mL (mean±SD=6.4±2.2 ng/ml, range from 2.7 to 9.1 ng/mL). Total PSA concentrations were measured using the Hybritech PSA assay on the Access Immunoassay System (Beckman Coulter, Inc., Brea, Calif.). Specimens were obtained prior to any diagnostic procedure or treatment and were stored at −70° C. prior to analysis.

N-Glycosylated Peptide Capture

Formerly N-linked glycosylated peptides were isolated from serum using the N-linked glycopeptide capture procedure as described previously (19,20). Briefly, 20 µl of individual serum or pooled serum was used for glycopeptide isolation. To prepare tryptic peptides from serum proteins, proteins from 20 µl of patient serum (~1 mg total protein) were first denatured in 90 µl of 8M urea, 0.4 M $NH_4HCO_3$, and 0.1% SDS for 2 hours at 60° C. The peptides were then reduced by adding 10 µl of 120 mM Tris(2-carboxyethyl) phosphine at room temperature for 30 min and alkylated by mixing with 10 µl of 160 mM iodoacetamide at room temperature for 30 min in the dark. Each sample was diluted by 190 µl of trypsin digestion buffer (100 mM $KH_2PO_4$, pH 7.4) with 20 µg of trypsin, and the proteins were digested at 37° C. overnight with gentle shaking. The digested peptides were cleaned with C18 columns and oxidized by adding 45 µl of 100 mM sodium periodate in 50% acetonitrile at 4° C. for 1 hour in the dark. After removal of the oxidant using C18 columns, the sample was conjugated to hydrazide resin at room temperature for 4 hours in 80% acetonitrile. Non-glycosylated proteins were then removed by washing the resin three times each with 800 µl of 1.5M NaCl, $H_2O$, and 100 mM of $NH_4HCO_3$. Then, N-linked glycopeptides were released from the resin by addition 2.5 mU of PNGase F in 100 mM of $NH_4HCO_3$ and incubated at 37° C. overnight. After the final clean up by MCX columns, the peptides were dried and resuspended in 20 µl of 0.4% acetic acid solution. The 20 µl of glycopeptide mixtures from 20 µl of original sera were used in each HPLC-MS analysis.

Synthesis of Stable Isotope Labeled Peptides

For glycopeptides identified from prostate tumor tissues using ABI 4800 MALDI TOF/TOF analyzer, the list of 8 peptides was selected for synthesis with heavy-isotope labeling (Table 1).

Peptides were synthesized at 2 µmol scale in a 96-well plate with an Intavis MultiPep synthesizer (Koeln, Germany). A heavy isotope form of aspartic acid was incorporated into all peptides during synthesis through the use of L-aspartic acid-N-Fmoc, beta-O-tert butyl ester (13C, 98%; 15N, 98%), which increased the peptide mass by 5 (Cambridge Isotope Laboratories, CNLM-4752, Andover, Mass.). Pre-loaded TentaGel S resins were from Rapp Polymere (Tübingen, Germany). Amino acids activated in situ with 1-H-benzotriazolium, 1-[bis(dimethylamino)methylene]-hexafluorophosphate(1-),3-oxide:N-methylmorpholine were coupled at a 5-fold molar excess over peptide. Each coupling cycle was followed by capping with acetic anhydride to avoid accumulation of one residue deletion peptide byproducts. After synthesis, peptide-resins were treated with a standard trifluoroacetic acid-tri-isopropyl silane-water cleavage solution and the peptides were precipitated by addition to cold ether. Four wells on the plate were used as synthesis controls, and these peptides along with some others were characterized by reversed-phase C18 HPLC (Waters DeltaPrep, Milford, Mass.), MALDI-TOF mass spectrometry (Biflex III, Bruker Daltonics, Billerica, Mass.), and ion trap (LCQ DecaXP, ThermoFinnigan, San Jose, Calif.) MS. The absolute amounts of reference peptides were unknown since synthetic peptides were not quantified by amino acid analysis. However, the peptide amount for each standard peptide was carefully titrated to the lowest amount needed for detection using TOF/TOF analyzer, and the spike-in amount of standard peptides was exactly same for each serum sample. This ensured that the maximum loading of serum glycopeptides and relative abundance of the native peptides from serum samples could be determined using this method.

2D-HPLC Fractionation and MS Analysis

For each 2D-LC run, 20 µl of the glycopeptides spiked with heavy-isotope-labeled-peptide standard peptide mixtures were separated with strong-cation-exchange (SCX) and reverse phase (RF) columns, and spotted on a MALDI plate. The glycopeptide mixtures were first separated by SCX column (300-µm inner diameter×15 cm long) using salts plugs (50 µl of 0, 5, 50, and 500 mM KCl solution) to elute peptides at a flow rate of 10 µl/min. The eluted peptides were trapped on a C-18 trap column (300-µm inner diameter×5 cm long) and then separated by a nano-scale C-18 reverse phase column (75-µm inner diameter×15 cm long) at a flow rate of 300 nl/min. The HPLC mobile phase A and B were 0.1% TFA in HPLC grade water and 0.1% TFA, 5% isopropanol in HPLC grade acetonitrile, respectively. The mobile phase B was increased from 3% to 80% in 110 min. The eluent from the nano-RF-HPLC column was mixed with the α-cyano-4-hydroxycinnamic acid matrix solution in a 1:1 ratio in a mixing tee before spotting onto the MALDI plate. The fractions were automatically collected in 30-s intervals and spotted 192 spots for the first SCX fraction (salt plug=0 mM KCl) and 144 spots for the second, third, and forth SCX fractions (salt plug=5, 50, and 500 mM KCl) on a MALDI plate using an on-line MALDI spotter.

The created peptide arrays on MALDI plates were then analyzed by ABI 4800 MALDI-TOF/TOF tandem mass spectrometer. Both MS and MS/MS data were acquired with a Nd:YAG (neodymium doped yttrium aluminum garnet) laser and used the instrument default calibration. The obtained MS spectra were used for peptide quantification, while the MS/MS spectra were used for peptide identification and validation in this study. The MS/MS database searches were performed against the National Center for Biotechnology Information (NCBI) database using ABI GPS Explorer software.

PSA Sensitivity Test Using Glycopeptide Isolation and 2D-LC-MS

Different amounts of PSA protein from Calbiochem were mixed with healthy women (PSA concentration <0.01 ng/ml based on clinical PSA test) to prepare sensitivity test samples. The total PSA concentrations were measured using the Hybritech PSA assay on the Access Immunoassay System, and the prepared PSA concentrations were 0.01 ng/ml, 1.6 ng/ml, 3.44 ng/ml, 9.95 ng/ml, 26.87 ng/ml, and 51.43 ng/ml. PSA contains a single N-linked glycosylation site and tryptic digestion will result in peptides with only two amino acid that is too short to detect by mass spectrometer. We therefore digested PSA with Endoproteinase Arg-C. First, 50 ug of PSA was denatured in 100 µl of 8M urea and 0.4M of $NH_4HCO_3$. The protein was then reduced by adding 2 µl of 120 mM Tris(2-carboxyethyl)phosphine at room temperature for 30 min and alkylated by mixing with 2 µl of 160 mM iodoacetamide at room temperature for 30 min in the dark. The PSA was diluted by 100 ul Arg-C digestion buffer (100 mM Tris-HCl, 20 mM $CaCl_2$, 10 mM DTT, 1 mM EDTA, 40 mM Methylamine, adjust pH to 7.6). 1 ug proteinase Arg-C was added to digest protein at 37° C. overnight with gentle shaking.

The digested PSA peptide were added to trypsin solution digested pooled serum from healthy women using the same dilution factor as spiking PSA proteins to healthy woman's serum. The glycopeptides were isolated from the serum samples and re-suspended in 40 ul 0.4% acetic acid. A glycopeptide mixture isolated from 40 ul of healthy women serum without spike-in PSA was prepared as negative control. 1 ul of 1:1000 diluted heavy peptide N*KSVILLGR (SEQ ID NO: 9) (N* represents the N-linked glycosylation site and is converted to D after deglycosylation. It is labeled with heavy isotope) was added into each sample and analyzed by 2D-LC-MALDI-MS using the method as described previously.

Data Export from 2D-LC-MALDI-TOF/TOF

MS and MS/MS spectra information for each sample was exported as binary files with the ABI Peak Explorer software, respectively. MS spectra files were then processed by a customized conversion tool for extracting the peptide peak information that includes sample name, spot number, peptide mass, mono-isotopic peak area, cluster peak area, and signal to noise ratio. The MS/MS spectra files were processed with the same procedure; and the extracted MS/MS peak information including sample name, spot number, peptide precursor mass, fragment ion mass, and signal to noise ratio of each fragment ion peak.

Detection of Target Peptides

The following procedure was applied to detect the targeted peptides in serum samples using heavy-isotope-labeled-peptide standards and their results were reported in Table 1.

Peptides were first detected using chromatography co-elution from MS spectra. In this approach, we developed a software tool to extract data from the exported data generated with 2D-LC-MALDI-TOF/TOF-MS and identify the native and heavy-isotope-labeled-peptide pairs. First, the software constructed a reference table for all native and heavy-isotope-labeled peptides using their calculated mass. Second, peaks with a signal to noise ratio more than 20 from 2D-LC-MALDI-TOF/TOF-MS were select to determine peptide pairs with co-elution of native and its corresponding heavy-isotope-labeled peptide at the same spot. Finally, each pairs were further validated with targeted acquisition of MS/MS spectra and identified with one of the following fragment ions matching method (see below).

Peptide pairs were further verified using precursor and fragment ion matching. In this approach, we matched fragment ions of the targeted peptide pairs with their theoretical fragment ions. Based on the organized MS/MS peak information, the identification procedure consists of the following four steps: 1) Calculate fragment ions for the 8 pairs of standard and native peptides based on their amino acid sequence (Table 1); 2) Search for all qualified peptide pairs by matching their associated MS/MS peaks with their theoretical fragment ions; 3) Assign the fragment ion types and positions for a, b, c, x, y, and z ions associated with their corresponding amino acids sequences. 4) Order the dataset, which contains all matched fragment ion types and positions, sample names, fraction numbers, and the spot numbers. Then perform a search for peptides with fragment ions matching to a series of amino acid fragment ions. This study requires at least two same data points for each peptide pair to confirm a final identification of one sequence.

Peptides were identified using Mascot Search from MS/MS spectra. In this identification method, the MS/MS spectra obtained were used. The MS/MS database search was performed against the public database (NCBI) using the GPS Explorer™ Software (Applied Biosystems) with the Mascot® Search Engine. The parameters for the database search are as follows: 1) The mass tolerance of the precursor was set at 200 ppm; 2) The mass tolerance of the fragment ion was ±0.6 Da; and 3) Presence of protein modifications including carboxymethylation of cysteines, oxidation of methionines, and an enzyme-catalyzed conversion of asparagine to aspartic acid at glycosylated site. Then, the dataset was further filtered to ensure that all the identified peptides have the Mascot peptide ion score greater than 90%.

Analysis of Target Peptides in Prostate Cancer Serum

The detection and quantitation of target peptides in each serum sample was determined by computing the monoisotopic peak area of each peptide pair found in all fractions and determining of the relative peptide abundances of each native peptide to its corresponding heavy-isotope-labeled peptide.

Proteins Preferentially Expressed in Prostate Tumor

In our previous study, we analyzed N-linked glycopeptides from prostate tumor tissues and identified 445 unique N-linked glycosites (8,21). A glycopeptide database, UniPep, was established that contains predicted N-linked glycopeptides from human proteome and glycopeptides identified from different body fluids, cancer tissues, and cells as resources for biomarker discovery (22). From these data, we compared the N-linked glycosites identified form prostate cancer tissues with those identified from other tissues and cells (ovarian cancer tissues and cells, breast cancer tissues and cells, bladder cancer tissues, liver cancer tissues, and lymphocyte cells) and identified eight glycoproteins that are highly expressed in prostate tissues by comparing frequency of MS/MS spectrum from prostate tumor to that of other tumor tissues or cells (Table 1). These included Kallikrein 11, Prostate stem cell antigen, Prostate specific antigen, Prostatic acid phosphatase, Olfactomedin 4, Metalloproteinase inhibitor 1, Membrane metallo-endopeptidase, and Gamma-glutamyltranspeptidase 1 (Table 1).

We next sought to determine whether the preferential expression of these glycoproteins from the proteomic study could be observed mRNA levels. Using microarray data of these glycoproteins from available published microarray analyses, we analyzed the gene expression pattern of these same glycoproteins in other tissues and cells (23,24). We found that the gene expression of these glycoproteins were at least 5-fold of the median value for 64 tissues or cells used (23,24) (Table 1). This indicated that these glycoproteins were preferentially expressed in prostate from both proteomic data and gene expression data (Table 1).

2D-LC-MALDI-TOF/TOF-MS Platform for Detection of Prostate Tumor Proteins in Sera To determine which glycopeptides can be detected in sera of prostate cancer patients, the 8 glycopeptide sequences were selected for synthesis of heavy-isotope-labeled-peptide standards. Table 1 lists the sequences of the 8 synthesized heavy-isotope-labeled peptides as standards.

We next set up the process for detection and quantitation of N-linked glycopeptides from prostate cancer tissues in serum samples to include the following six steps (FIG. 1): Spiking in: N-linked glycopeptides from each serum sample were mixed with the same amount of mixture of 7 heavy-isotope-labeled-peptide standards except PSA (Table 1). Separation: the combined peptide solution was fractionated by a 2D Nano-HPLC system using SCX and RP chromatography as the first and the secondary dimensional separations. The eluted peptides were continuously deposited on a MALDI plate to create a peptide array. Analysis: the peptide array was then analyzed by a MALDI-TOF/TOF mass spectrometer. Detection: the native peptide from the serum samples and the corresponding synthetic peptide were detected as paired peaks with 5 Dalton mass differences on MS spectra. Validation: To further verify the selected pairs, the target peptide pairs were then selected to generate tandem mass spectra. The generated MS/MS data was analyzed using an in-house developed software tool to confirm the selected peptides using MS/MS spectra. Quantitation: the abundance of targeted peptides in each sample was determined based on the ratio of mono-isotopic peak areas of the native peaks to the synthetic peaks.

To increase the sensitivity of detecting prostate tumor proteins in patients' sera, we optimized this platform by maximizing sample loading of serum glycopeptides. First, the 2D-HPLC configuration and separation conditions for maximal loading and glycopeptide separation were optimized using the high resolution columns, the 4 fractions of SCX, and the RP gradients of mobile phase. Using the described method per experiment, we can load 40 µg of peptides for each analysis. Second, to further maximize the loading of serum peptides, we determined the minimum amount of each heavy-isotope-labeled peptide needed as standard to spike in the serum samples for MS detection. Finally, sample loading of glycopeptides from 20 µL of human serum was determined to be analyzed for each run under the optimized 2D-LC-MALDI-TOF/TOF-MS Method.

Detection of PSA Level Using Glycopeptide Isolation, Heavy-Isotope-Labeled-Peptide Standards, and 2D-LC-MALDI-TOF/TOF-MS Analysis It is well known that proteins from specific tumor are largely diluted by the total serum volume and masked by high abundance proteins in serum when these proteins are released from tissue into blood. As a result, most serum tumor markers currently in clinical use, such as known prostate cancer marker, PSA, have concentrations in the ng/ml range. Therefore, proteomic technologies for tumor biomarker discovery from serum need to achieve this sensitivity. However, none of the conventional proteomic methods have been able to shown the detection of tumor serum markers such as PSA in serum (25). Recently, Steven Carr group demonstrated an ultra-sensitive detection method combing high abundance plasma protein depletion, multiple reaction monitoring, and stable isotope dilution mass spectrometry (26). The detection limit of specific proteins was below the ng/ml in plasma. However, the limit of quantitation was about 25 ng/ml for PSA due to the interference from plasma in the m/z transitions. So, we first investigated the sensitivity of the glycopeptide isolation, heavy-isotope-labeled-peptide standards, and 2D-HPLC-MS analysis for PSA detection.

PSA has a single N-linked glycosylation site. However the glycopeptide from this site, N*KSVILLGR (SEQ ID NO: 10) (N* represents the N-linked glycosylation site) would not be detected from patients' sera if trypsin were used to isolate the N-linked glycopeptide. This is due to the fact that the N-linked glycosylation site of PSA is surrounded by two tryptic cleavage sites in both directions. Therefore, the complete tryptic digestion of the N-linked glycopeptide from PSA produces only two amino acids which are not detectable by MS. We therefore used proteinase Arg-C to digest PSA protein to obtain N-linked glycopeptide (N*KSVILLGR) (SEQ ID NO: 10). After digestion of PSA with Arg-C, solutions with known amount PSA were spiked in the pooled tryptic peptides from pooled serum form healthy women to prepare total PSA concentrations of 0.01 ng/ml, 1.6 ng/ml, 3.44 ng/ml, 9.95 ng/ml, 26.87 ng/ml, and 51.43 ng/ml. The same amount of synthetic heavy peptide dKSVILLGR (SEQ ID NO: 3) was added to each sample to detect, identify and quantify the corresponding native peptides based on the chromatography elution time, MS/MS fragment ions, and mono-isotopic peak ratio. As shown in FIG. 2, the lowest detectable concentration of PSA was 3.4 ng/ml and the linear detection range was from 3.4 gn/ml to 51.43 ng/ml (No data was availed higher than 100 ng/ml). The native peptide and corresponding heavy peptide were co-eluted on the same spot under 2D-HPLC separation. 4 fragment ions (Y1, Y3, Y5, and Y8) were observed at heavy peptide MS2 spectrum and 3 same fragment ions (Y1, Y5, Y8) were observed at native peptide MS2 spectrum. Both MS1 and MS2 spectra were shown at FIG. 2. Detection of glycopeptides from the known concentration of PSA indicates that low abundant glycopeptides/proteins with clinical relevance can be directly identified in serum by combining glycopeptide capture, heavy-isotope-peptide standards, and 2D-LC-MALDI-TOF/TOF-MS platform. This is the first study that demonstrates that mass spectrometry can be used to sensitively detect low abundance PSA in serum.

Detection of N-Linked Glycopeptides Identified from Prostate Tumor Tissues in Serum.

To determine which of the rest 7 glycoproteins from prostate tumor (Table 1) can be detected in sera from cancer patients with early stage prostate cancer (PSA levels less than 10 ng/ml), we analyzed 9 individuals with confirmed biopsy-positive prostate cancer. The N-linked glycopeptides from 20 µL of individual serum samples were mixed with 7 heavy-isotope-labeled-peptide standards, then separated using 2D (SCX and RP) chromatography and spotted (624 spots) on MALDI targets. The mass of the peptides on MALDI target plates was measured with the ABI-4800 mass spectrometer.

We first determined which heavy-isotope-labeled-peptide standards can be detected in serum after spiking in glycopeptides by searching the MS data using their mass. We found that all 7 targeted heavy-isotope-labeled peptides spiked into the serum samples could be detected with the peptide mass accuracy within 200 ppm.

We then detected native glycopeptides from serum containing the same peptide sequences as the heavy-isotope-labeled peptide standards. Since each formerly N-linked glycopeptide contains the D converted from formerly N-linked glycosylated N, in the synthetic peptide sequence, one N from each peptide was replaced with heavy $^{13}$C-and $^{15}$N-labeled D to create a mass difference of 5 Dalton between the light native peptide and heavy-isotope-labeled-peptide standards. The synthetic peptide retains the same physical characteristics of the native peptide including the same chromatographic retention time, ionization efficiency, and CID fragmentation pattern except for the 5 mass unit difference. The chromatographic retention time was first selected to verify the native peptides using synthetic peptides based on the assumption that both native and synthetic peptides are able to co-elute on same spot during the 2D chromatography separation. To combine the peptide mass and the peptide retention time, 4 targeted native peptides were co-eluted with its corresponding heavy-isotope-labeled peptide from serum (Table 1).

Figures 1A, 3:
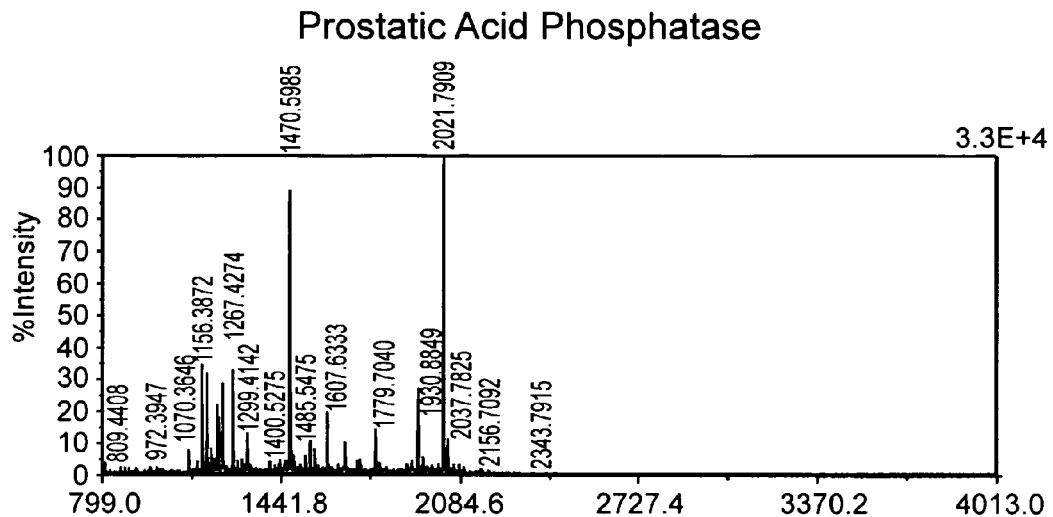
FIG. 3: Identification and quantification of glycopeptides from Prostatic acid phosphatase (PAP) (3-1) (SEQ ID NOS: 11 and 12, respectively, in order of appearance), Metalloproteinase inhibitor 1 (3-2) (SEQ ID NOS: 13 and 14, respectively, in order of appearance), Membrane metallo-endopeptidase (3-3) (SEQ ID NOS: 15 and 16, respectively, in order of appearance), Gamma-glutamyltranspeptidase 1 (3-4) (SEQ ID NOS: 17 and 18, respectively, in order of appearance) in serum with heavy-isotope-labeled-peptide standard and a 2D-LC MALDI-TOF/TOF-MS platform. A) The peptides on each spot of LC-MALDI plate were initially analyzed with MS scan to detect the peptides from serum that are paired with the heavy-isotope-labeled-peptide standards and quantify the peptide abundance. The abundance of each peptide was analyzed by comparison of the mono-isotopic peak area of the native peptide from serum to the heavy-isotope-labeled peptide. B) A enlargement of the peptide pairs from MS spectra with native peptide sequence and heavy peptide sequence. C) and D) MS/MS spectra of native peptide and heavy-isotope-labeled peptide were used to confirm the peptide sequence. (N*:N-linked glycosylation site and was converted to D after deglycosylation). (#: heavy-isotope-labeling aspartic acid)
Figures 1B, 3:
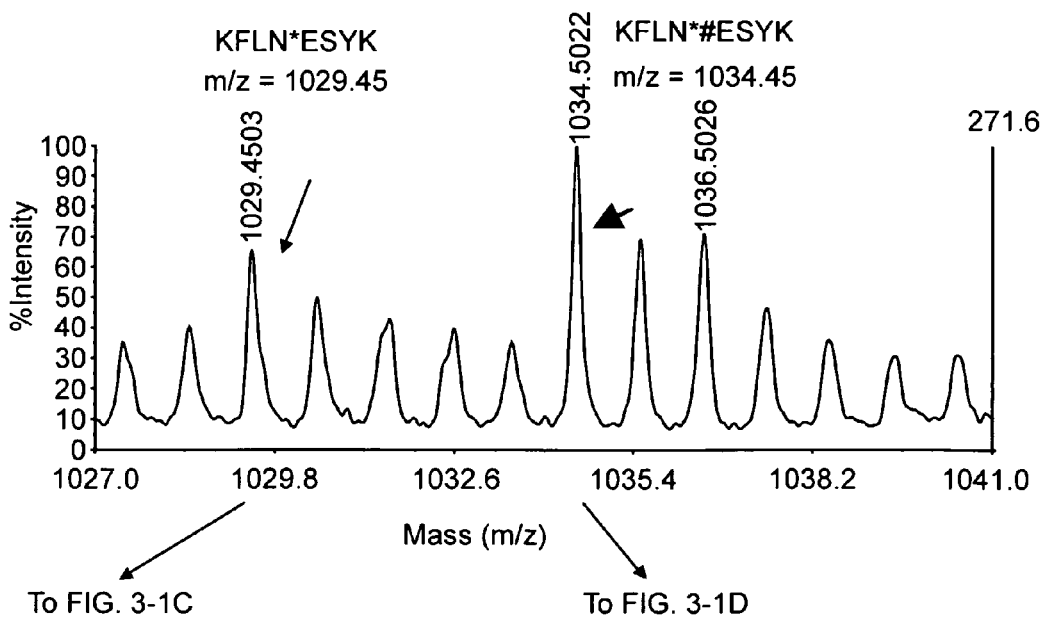
Figures 2A, 3:
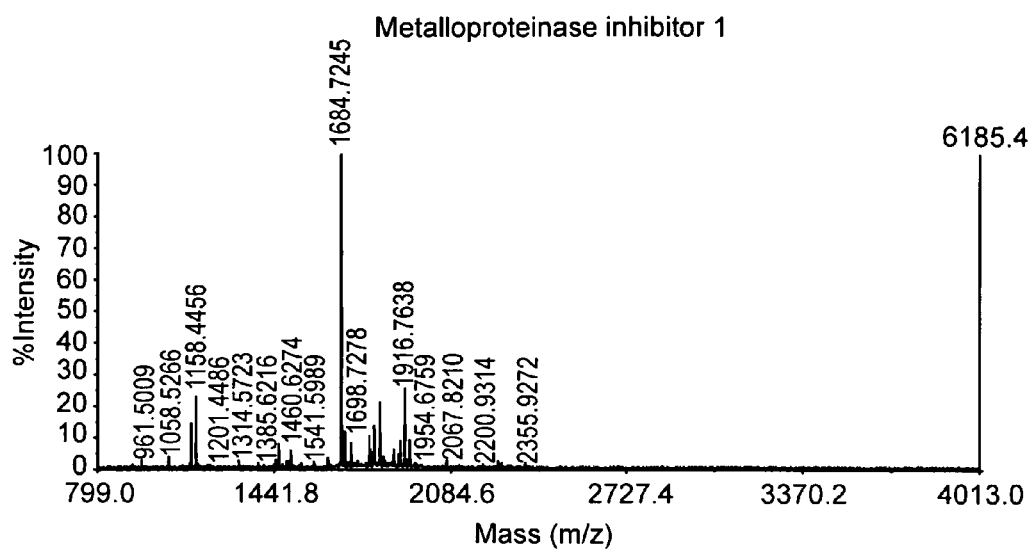
Figures 2B, 3:
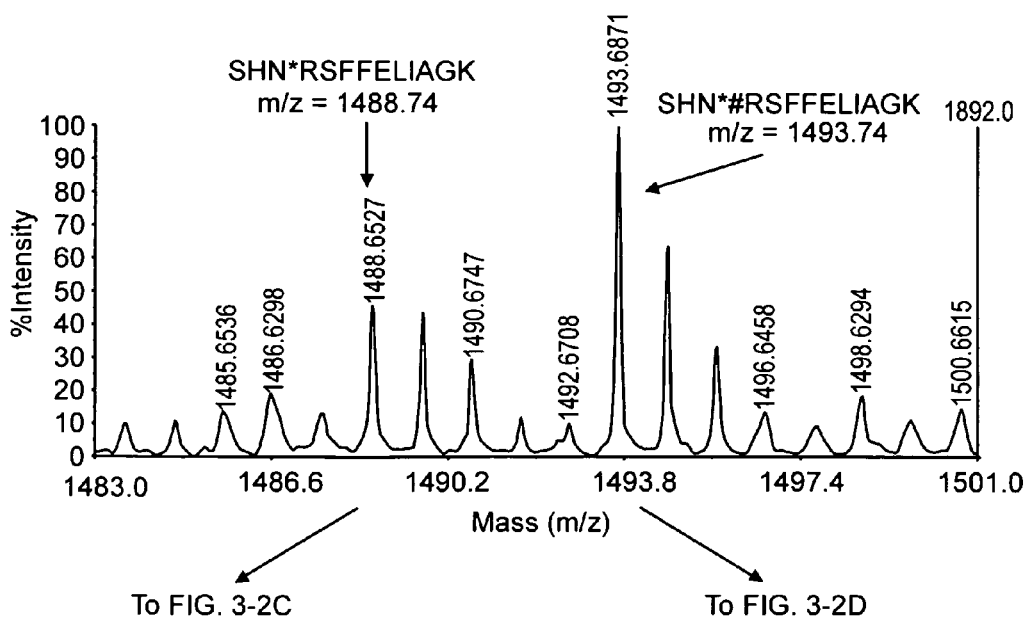
Figures 2C, 2D, 3:
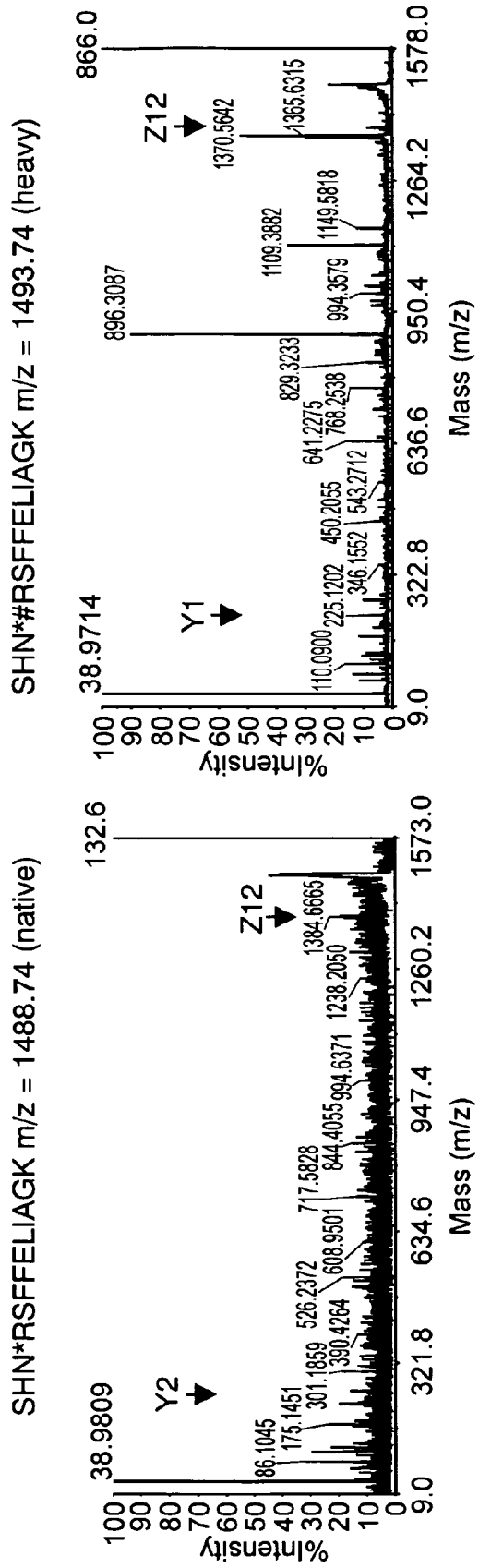
Figures 3, 3A:
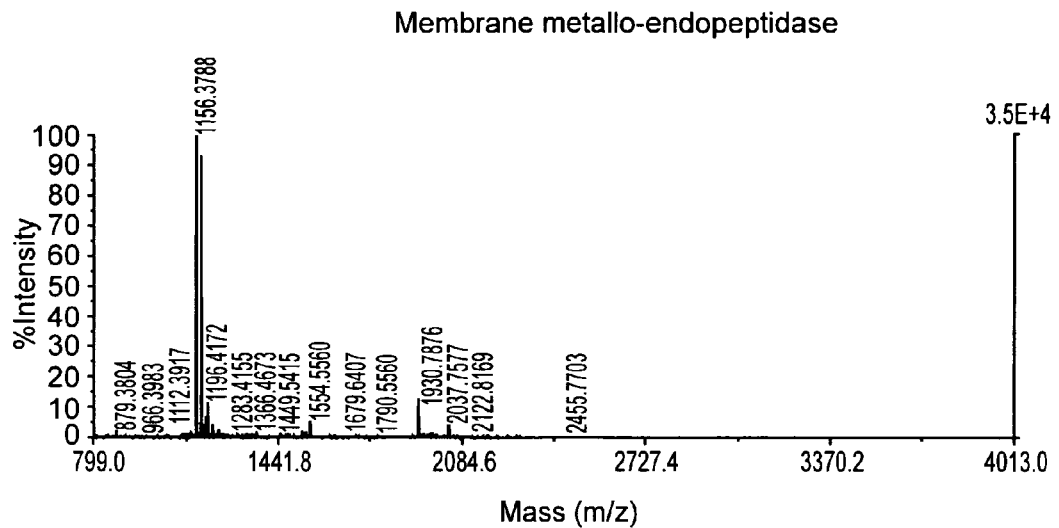
Figures 3, 3B:
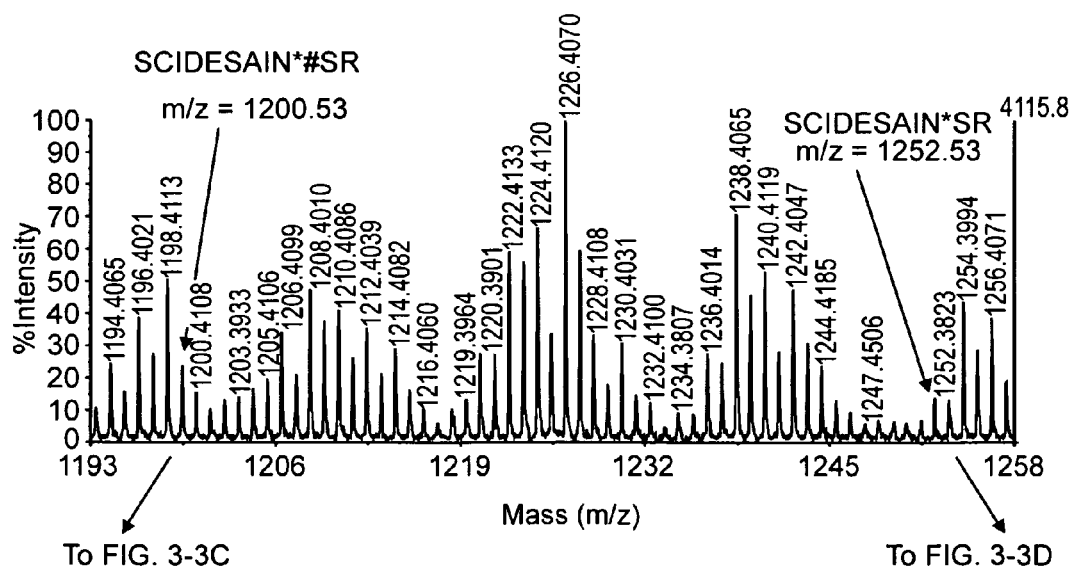
Figures 3, 3C, 3D:
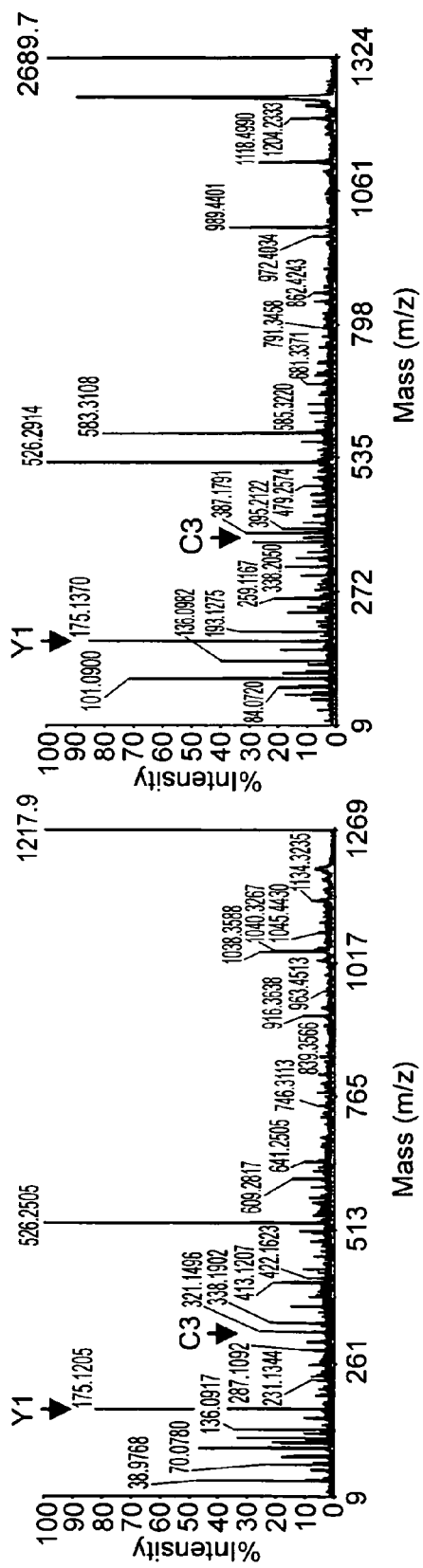

To verify the 4 detectable target peptides from serum samples using matched mass and co-elution, the CID spectra from the native peptide and its corresponding heavy-isotope-labeled peptide were compared to search for the same fragment ion peaks. The peptides with at least 2 same fragment ions matched on both native and heavy peptides are reported in Table 1. Using these criteria, we successfully validated the four peptide pairs in serum (Table 1, and FIG. 3). The 4 glycopeptides were selected as serum detectable prostate glycopeptides for further quantitative analysis.

Quantitative Analysis of Prostate Tumor N-Linked Glycopeptides in Sera from Two Groups of Individuals with Biopsy-Positive and Biopsy-Negative Results.

We then determined relative quantity of the N-linked glycopeptides in patients with PSA levels less than 10 ng/ml in biopsy-positive and negative groups. The glycopeptides captured from blood sera from 9 biopsy-positive prostate cancer patients and 10 biopsy-negative individuals were analyzed using a 2D-LC-MALDI-TOF/TOF-MS platform. The same amount of synthesized heavy-isotope-labeled-peptide standards were spiked into each glycopeptide isolated from each serum sample to determine the relative peptide abundances in individual samples. A set of specifically developed software tools for peptide identification and quantification was used to interpret the mass spectrometer MS and MS/MS data.

Figures 3, 4, 4A:
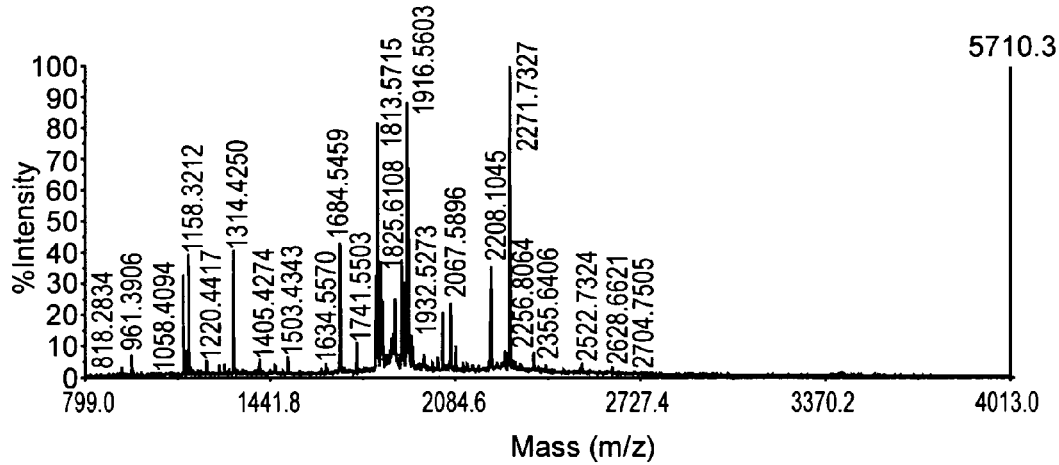
FIG. 4: Quantitative analysis of targeted glycopeptides in sera from biopsy positive and negative groups. Glycopeptide abundances in biopsy-negative (▲) and positive (●) groups. (1);Prostatic acid phosphatase (PAP) (SEQ ID NO: 3); (2): Metalloproteinase inhibitor 1 (SEQ ID NO: 6); (3):Membrane metallo-endopeptidase (SEQ ID NO: 7). (N*:N-linked glycosylation site and was converted to D after deglycosylation).
Figures 3, 4, 4B:
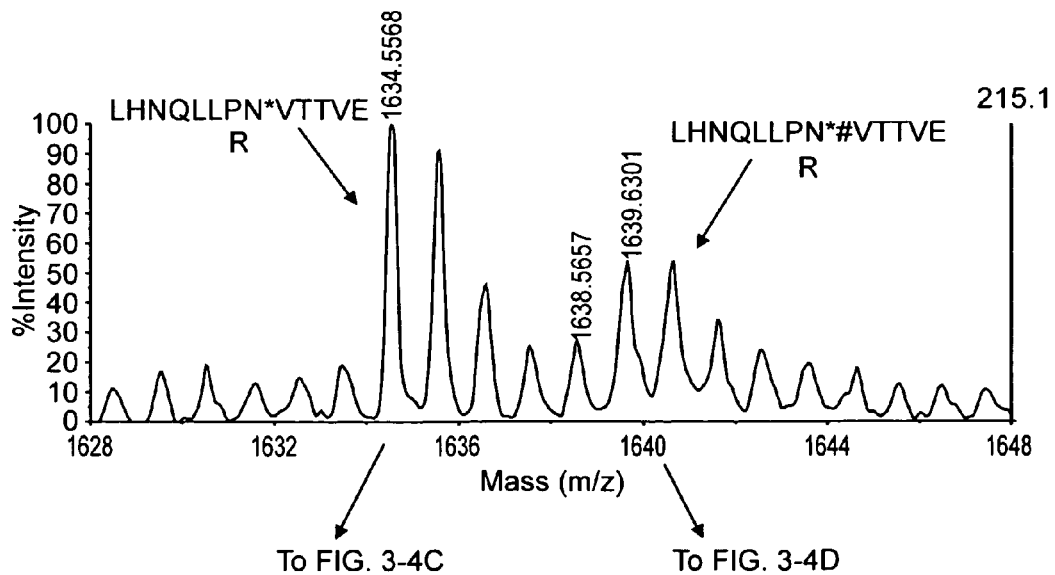
Figures 3, 4, 4C, 4D:
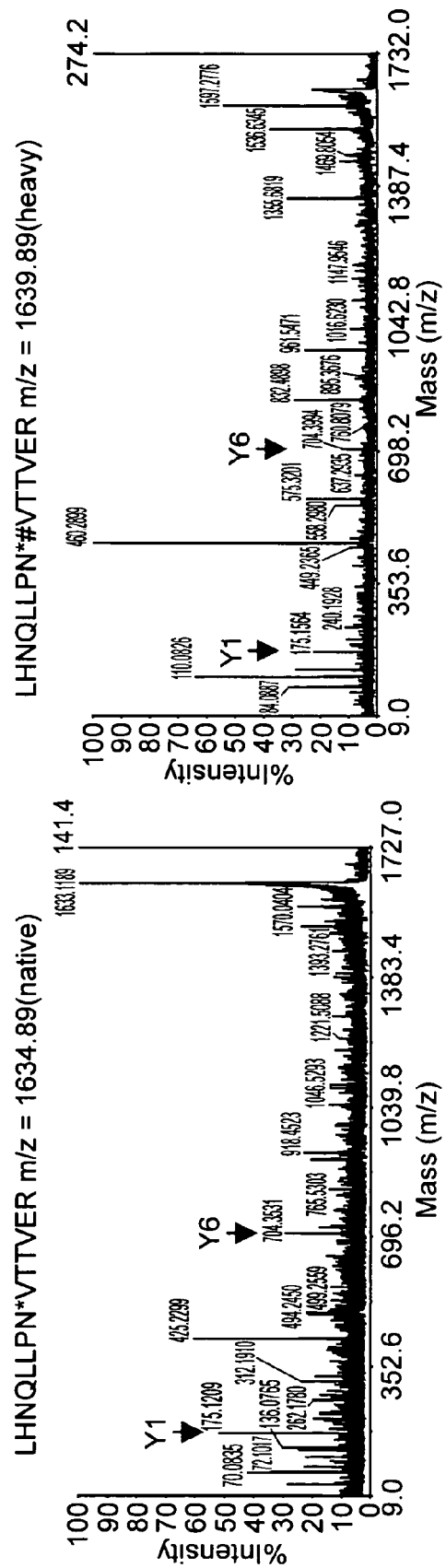

To determine relative glycopeptide abundance in each serum sample, we analyzed each target peptide using glycopeptides isolated from individual sera spiked-in with heavy-isotope-labeled-peptide standards. The relative abundance of each peptide from individuals was determined by the ratio of mono-isotopic peak area of native and heavy-isotope-labeled-peptide standards. FIG. 4 shows the distribution of the peptide abundance in biopsy-positive and -negative groups.

We found two of the prostate-specific glycoproteins, PAP and MME, were elevated in serum samples from biopsy positive prostate cancer patients (FIG. 4)

In the present study, we identified prostate tumor proteins and determined their detectability in the blood of prostate cancer patients. In this proteomic analysis, we successfully detected the majority of prostate cancer glycopeptides in serum and proved the assumption that proteins from cancer tissues can be detected in patient sera using mass spectrometry.

We chose to analyze the N-linked glycopeptide subproteome from both prostate cancer tissues and blood serum using synthetic peptide standards and 2D-LC-MALDI-TOF/TOF-MS. We demonstrated that cancer specific markers from cancer tissue can be analyzed in serum by mass spectrometry. Three factors might contribute to the sensitivity. First, most secreted proteins or cell surface proteins are glycosylated and likely deposited or shed to blood, the majority of currently known cancer biomarkers are known to be glycosylated (14). By focusing on glycopeptides from both cancer tissues and serum, the same subset of proteins/peptides identified from cancer tissues are also targeted in serum. In addition, glycopeptide capture largely reduces the complexity of the whole serum by removing most of the high abundance serum peptides and efficiently concentrates glycopeptides from crude serum samples. It significantly improved the analytical sensitivity compared with the analysis of whole serum samples (10). Second, the 2D-LC-MALDI-TOF/TOF-MS platform allows the targeted peptides to be specifically detected by MS and validated with MS/MS. It also increases the total volume of serum sample that can be analyzed for each run and increase the detection limit of low abundance prostate cancer peptides. Finally, the targeted approach using heavy-isotope-labeled-peptide standards increases the sensitivity and confidence of peptide detection. As the result, the sensitivity of the analysis was significantly improved and the detection limit has been demonstrated down to ng/ml scale. However, the throughput of the current experimental procedures was still sufficient for quantitative analysis of hundreds of targeted peptides with a throughput of two samples per day.

Co-elution of native serum peptides with heavy-isotope-labeled-peptide standards and fragment ion matching of the co-eluted peptides were used to detect and validate the detected peptides. Identification of serum peptides by searching the MS/MS spectra provides reliable results and allows the identification of novel sequences. However, database searching requires sufficient amount of peptides to generate enough information-rich MS/MS spectra to identify peptide sequence. It failed to efficiently identify most of prostate specific peptides in serum mainly due to two factors. First, the most of N-linked glycopeptides from prostate specific proteins were largely diluted when these proteins were released from tissue to blood serum. Secondly it is affected by the complexity of serum which is dominated by few high abundant plasma proteins, with albumin alone representing over 50% of the total protein content and another 25% of serum proteins are represented by the immunoglobulins (10). As the result, most prostate specific proteins were present at very low levels in blood and could not be efficiently identified using database searching method.

The heavy-isotope-labeled-peptide standards developed in this study could be used to verify and quantify many plasma proteins via MS using a high-throughput platform as recently demonstrated (11). This is a gel-free and antibody-free approach utilizing peptide and mass spectrometry for peptide validation and quantification of high throughput proteomic results.

In conclusion, this example demonstrates that glycopeptides originating from prostate cancer tissue could be detected in patients' sera and used as biomarkers for prostate cancer diagnosis.

REFERENCES

1. Etzioni, R., Urban, N., Ramsey, S., McIntosh, M., Schwartz, S., Reid, B., Radich, J., Anderson, G., and Hartwell, L. (2003) *Nat Rev Cancer* 3(4), 243-252
2. Aebersold, R., Anderson, L., Caprioli, R., Druker, B., Hartwell, L., and Smith, R. (2005) *J Proteome Res* 4(4), 1104-1109
3. Anderson, N. L. (2005) *Mol Cell Proteomics* 4(10), 1441-1444
4. Petricoin, E. F., Ardekani, A. M., Hitt, B. A., Levine, P. J., Fusaro, V. A., Steinberg, S. M., Mills, G. B., Simone, C., Fishman, D. A., Kohn, E. C., and Liotta, L. A. (2002) *Lancet* 359(9306), 572-577
5. Petricoin, E. F., 3rd, Ornstein, D. K., Paweletz, C. P., Ardekani, A., Hackett, P. S., Hitt, B. A., Velassco, A., Trucco, C., Wiegand, L., Wood, K., Simone, C. B., Levine, P. J., Linehan, W. M., Emmert-Buck, M. R., Steinberg, S. M., Kohn, E. C., and Liotta, L. A. (2002) *J Natl Cancer Inst* 94(20), 1576-1578
6. Coombes, K. R. (2005) *Clin Chem* 51(1), 1-2
7. Vejda, S., Posovszky, C., Zelzer, S., Peter, B., Bayer, E., Gelbmann, D., Schulte-Hermann, R., and Gerner, C. (2002) *Mol Cell Proteomics* 1(5), 387-393
8. Zhang, H., Liu, A. Y., Loriaux, P., Wollscheid, B., Zhou, Y., Watts, J. D., and Aebersold, R. (2007) *Mol Cell Proteomics* 6(1), 64-71
9. Zhang, H., Li, X. J., Martin, D. B., and Aebersold, R. (2003) *Nat Biotechnol* 21(6), 660-666
10. Zhang, H., Yi, E. C., Li, X. J., Mallick, P., Kelly-Spratt, K. S., Masselon, C. D., Camp, D. G., 2nd, Smith, R. D., Kemp, C. J., and Aebersold, R. (2005) *Mol Cell Proteomics* 4(2), 144-155
11. Pan, S., Zhang, H., Rush, J., Eng, J., Zhang, N., Patterson, D., Comb, M. J., and Aebersold, R. (2005) *Mol Cell Proteomics* 4(2), 182-190
12. Kuster, B., Schirle, M., Mallick, P., and Aebersold, R. (2005) *Nat Rev Mol Cell Biol* 6(7), 577-583
13. Presti, J. C., Jr. (2007) *Nat Clin Pract Urol* 4(9), 505-511
14. Ludwig, J. A., and Weinstein, J. N. (2005) *Nat Rev Cancer* 5(11), 845-856
15. Babaian, R. J., Johnston, D. A., Naccarato, W., Ayala, A., Bhadkamkar, V. A., and Fritsche, H. H., Jr. (2001) *J Urol* 165(3), 757-760
16. Ankerst, D. P., and Thompson, I. M. (2007) *J Urol* 177(2), 426-427
17. Thompson, I. M., Pauler, D. K., Goodman, P. J., Tangen, C. M., Lucia, M. S., Parnes, H. L., Minasian, L. M., Ford, L. G., Lippman, S. M., Crawford, E. D., Crowley, J. J., and Coltman, C. A., Jr. (2004) *N Engl J Med* 350(22), 2239-2246
18. Sokoll, L. J., Chan, D. W., Mikolajczyk, S. D., Rittenhouse, H. G., Evans, C. L., Linton, H. J., Mangold, L. A., Mohr, P., Bartsch, G., Klocker, H., Horninger, W., and Partin, A. W. (2003) *Urology* 61(2), 274-276
19. Tian, Y., Zhou, Y., Elliott, S., Aebersold, R., and Zhang, H. (2007) *Nat Protocols* 2, 334-339
20. Zhou, Y., Aebersold, R., and Zhang, H. (2007) *Anal Chem* 79(15), 5826-5837
21. Liu, A. Y., Zhang, H., Sorensen, C. M., and Diamond, D. L. (2005) *J Urol* 173(1), 73-78
22. Zhang, H., Loriaux, P., Eng, J., Campbell, D., Keller, A., Moss, P., Bonneau, R., Zhang, N., Zhou, Y., Wollscheid, B., Cooke, K., Yi, E. C., Lee, H., Peskind, E. R., Zhang, J., Smith, R. D., and Aebersold, R. (2006) *Genome Biol* 7(8), R73
23. Su, A. I., Wiltshire, T., Batalov, S., Lapp, H., Ching, K. A., Block, D., Zhang, J., Soden, R., Hayakawa, M., Kreiman, G., Cooke, M. P., Walker, J. R., and Hogenesch, J. B. (2004) *Proc Natl Acad Sci USA* 101(16), 6062-6067
24. Su, A. I., Cooke, M. P., Ching, K. A., Hakak, Y., Walker, J. R., Wiltshire, T., Orth, A. P., Vega, R. G., Sapinoso, L. M., Moqrich, A., Patapoutian, A., Hampton, G. M., Schultz, P. G., and Hogenesch, J. B. (2002) *Proc Natl Acad Sci USA* 99(7), 4465-4470
25. Diamandis, E. P. (2004) *Mol Cell Proteomics* 3(4), 367-378
26. Keshishian H, Addona T, Burgess M, Kuhn E, and Carr S A. (2007) *Mol Cell Proteomics* 6(12), 2212-2219

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of detecting prostate cancer in a subject, comprising:
   a. obtaining a serum sample from the subject;
   b. adding to the sample up to eight isotopically labeled peptides identical to native biomarker peptides derived from protease digestion of the biomarkers prostate specific antigen (KLK3), prostatic acid phosphatase (ACPP), metalloproteinase inhibitor 1 (TIMP1), membrane metalloendopeptidase (MME), and gamma-glutamyltranspeptidase 1 (GGT1), wherein the up to eight isotopically labeled peptides include SEQ ID NO:3, SEQ ID NO:4, SEQ ID NO:6, SEQ ID NO:7, and SEQ ID NO:8;
   c. detecting the presence of the isotopically labeled peptides and unlabeled, native biomarker peptides using mass spectrometry, wherein the presence of the native biomarker peptides in the sample is indicative of prostate cancer.

2. The method of claim 1, further comprising determining the amount of the native biomarker peptides in the sample.

3. The method of claim 1, wherein the subject has a PSA level of 10 ng/ml or less.

4. The method of claim 1, wherein the isotopically labeled peptides comprise a heavy isotope labeled aspartic acid.

5. The method of claim 1, further comprising isolating N-linked glycosylated peptides from the serum sample prior to step (b).

* * * * *

UNITED STATES PATENT AND TRADEMARK OFFICE
CERTIFICATE OF CORRECTION

PATENT NO. : 8,603,734 B2
APPLICATION NO. : 12/663191
DATED : December 10, 2013
INVENTOR(S) : Hui Zhang et al.

Page 1 of 1

It is certified that error appears in the above-identified patent and that said Letters Patent is hereby corrected as shown below:

In the Specification

Column 1, please replace the first paragraph as follows:
STATEMENT OF GOVERNMENTAL INTEREST
This invention was made with government support under grant number CA114852, CA111244, CA115102, awarded by the National Institutes of Health. The government has certain rights in the invention.

Signed and Sealed this
Twenty-fourth Day of April, 2018

Andrei Iancu
*Director of the United States Patent and Trademark Office*